(12) United States Patent
Siebenweiber et al.

(10) Patent No.: US 12,133,749 B2
(45) Date of Patent: Nov. 5, 2024

(54) BASE BODY OF A COMPUTED TOMOGRAPHY DRUM COMPRISING AT LEAST TWO SEPARATELY PRODUCIBLE COMPONENTS, COMPUTED TOMOGRAPHY DRUM AND COMPUTED TOMOGRAPHY DEVICE

(71) Applicant: Siemens Healthcare GmbH, Erlangen (DE)

(72) Inventors: Michael Siebenweiber, Kulmain (DE); Jan-Christoph Kiesel, Bayreuth (DE); Stefan Gross, Trabitz (DE); Ralf Gaertner, Kemnath (DE); Stefan Hesl, Eschenbach (DE); Klaus Hruschka, Erbendorf (DE); Alexander Kraemer, Irchenrieth (DE); Riccardo Kunze, Erlangen (DE); Wolfgang Neuber, Pressath (DE); Hubert Plannerer, Kemnath (DE); Rainer Reber, Reuth (DE); Guido Schraml, Schwarzenbach (DE); Fabian Strobl, Erbendorf (DE); Kerstin Waldbach, Porstendorf (DE)

(73) Assignee: SIEMENS HEALTHINEERS AG, Forchheim (DE)

(*) Notice: Subject to any disclaimer, the term of this patent is extended or adjusted under 35 U.S.C. 154(b) by 536 days.

(21) Appl. No.: 17/475,469

(22) Filed: Sep. 15, 2021

(65) Prior Publication Data

US 2022/0087621 A1 Mar. 24, 2022

(30) Foreign Application Priority Data

Sep. 24, 2020 (DE) ..................... 10 2020 212 026.9

(51) Int. Cl.
*A61B 6/00* (2024.01)
*A61B 6/02* (2006.01)
(Continued)

(52) U.S. Cl.
CPC .............. *A61B 6/035* (2013.01); *A61B 6/027* (2013.01); *A61B 6/0407* (2013.01)

(58) Field of Classification Search
CPC ....... A61B 6/027; A61B 6/035; A61B 6/0407; A61B 6/4429
See application file for complete search history.

(56) References Cited

U.S. PATENT DOCUMENTS

2011/0062354 A1 3/2011 Pettinato
2014/0119503 A1* 5/2014 Matsuzawa .............. H05G 1/02
378/197

OTHER PUBLICATIONS

Klocke Fritz "Fertigungsverfahren 4 Umformen", 6. Auflage, Chapter 4.4 (pp. 406-423), Springer Verlag, 2017; and English translation.
German Office Action mailed Apr. 15, 2021.

* cited by examiner

*Primary Examiner* — Dani Fox
(74) *Attorney, Agent, or Firm* — Harness, Dickey & Pierce, P.L.C.

(57) ABSTRACT

A base body of a computed tomography drum is disclosed. In an embodiment, the base body includes at least the following components: a base plate, an outer ring and an inner ring. The inner ring is arranged concentrically with the outer ring. The outer ring and the inner ring are arranged on the base plate. At least two of the components are configured as separately producible components. Two of the separately producible components are connected to one another by way of at least one of: bonding, welding, riveting, clinching, clinch-bonding and/or rivet-bonding.

24 Claims, 9 Drawing Sheets

(51) Int. Cl.
*A61B 6/03* (2006.01)
*A61B 6/04* (2006.01)

ND OF A COMPUTED
BASE BODY OF A COMPUTED TOMOGRAPHY DRUM COMPRISING AT LEAST TWO SEPARATELY PRODUCIBLE COMPONENTS, COMPUTED TOMOGRAPHY DRUM AND COMPUTED TOMOGRAPHY DEVICE

PRIORITY STATEMENT

The present application hereby claims priority under 35 U.S.C. § 119 to German patent application number DE102020212026.9 filed Sep. 24, 2020, the entire contents of which are hereby incorporated herein by reference.

FIELD

Example embodiments of the invention generally relate to a base body of a computed tomography drum comprising at least two separately producible components, a computed tomography drum and computed tomography device.

BACKGROUND

In medical imaging, computed tomography (CT) imaging belongs to the standard methods. For CT imaging, a patient is positioned in a center of rotation or on a rotation axis, about which at least one X-ray tube or X-ray source or radiation source and at least one X-ray detector or detector or radiation detector rotate. The X-ray tube and the X-ray detector are arranged opposite one another. In other words, the X-ray tube and the X-ray detector are arranged such that an X-ray radiation emitted by the X-ray tube penetrates the patient, interacts with the tissue of the patient and is subsequently acquired and/or detected by the X-ray detector. The X-ray tube and the X-ray detector are arranged, in particular, on a computed tomography (CT) drum. The CT drum is configured as an annular component. Therein, a base body of the CT drum forms the annular shape of the CT drum. In other words, the base body provides a fundamental shape of the CT drum. The CT drum or the base body forms a circular opening round the rotation axis in which the patient can be positioned. For the rotation of the X-ray tube and the X-ray detector, the CT drum and therefore also the base body rotates round the rotation axis. Herein, the CT drum and/or the base body typically rotates at approximately 250 revolutions per minute.

It is known to make the base body of the CT drum in a sand casting process, due to its size. Typically, an aluminum-silicon casting alloy is used for this. Typically, the base body is produced as a cast component or a cast part.

However, following the sand casting process, a complex machining of the base body is typically necessary. For example, a surface of the base body is often formed too rough by the sand casting process. In addition, a tolerance interval is high in the production of the base body by the sand casting process. Among other things, for smoothing the surface and for evening out the tolerances, the base body can be machined or postprocessed by metal-cutting device(s). When casting is used, faults that are difficult to discern, such as cavities and/or cracks, can occur. Such faults can also occur under the surface of the base body and can therefore be undetectable or detectable only with difficulty. Such faults can reduce the stability of the base body. In addition, as a result of the machining, stresses can be introduced into the base body by strain-hardening.

Furthermore, the aluminum-silicon casting alloy that is typically used for the sand casting process has a relatively low modulus of elasticity of approximately 70000 MPa. This leads, for example, in the region at which the X-ray tube is arranged on the CT drum, to a deformation of approximately 1 mm during the rotation. In order to prevent and/or reduce this, typically, stabilizers and/or coarse balancing weights and/or fine balancing weights are arranged on the base body.

In addition, a design change of the base body in the case of a base body made with a casting process, in particular, a sand casting process, can only be implemented with a great effort. A design change therein defines a change of the base body in its shape and/or geometrical configuration. A design change in the case of the sand casting process, is typically associated with an adaptation of a casting mold of the base body. In particular, an adaptation of the casting mold which is used for the sand casting process is complex and costly.

SUMMARY

At least one embodiment of the present invention provides a base body which has a greater stability during rotation, for the production of which a low postprocessing effort is necessary and which is easily adaptable to design changes.

Embodiments are directed to a base body of a computed tomography drum, a computed tomography drum and a computed tomography device. Advantageous developments are disclosed in the claims and in the following description.

At least one embodiment of the invention relates to a base body of a computed tomography drum. The base body comprising: a base plate, an outer ring and an inner ring. The inner ring is arranged concentrically with the outer ring. The outer ring and the inner ring are arranged on the base plate. At least two of the components are configured as separately producible components. Two of the separately producible components are connected to one another by way of at least one of the following methods: bonding, welding, riveting, clinching, clinch-bonding and/or rivet-bonding.

At least one embodiment of the invention further relates to a base body of a computed tomography drum, the base body comprising at least two mutually independently producible sectors. Therein, the sectors are cast components. Therein, the sectors are connected together to the base body.

At least one embodiment of the invention further relates to a computed tomography drum which comprises a base body, a fastening apparatus for an X-ray tube and a fastening apparatus for an X-ray detector.

At least one embodiment of the invention further relates to a computed tomography device comprising a computed tomography drum, an X-ray tube, an X-ray detector, a drive for a rotation of the computed tomography drum and a patient support.

At least one embodiment of the invention further relates to a base body of a computed tomography drum, comprising components including:
 a base plate;
 an outer ring; and
 an inner ring, the inner ring being arranged concentrically with the outer ring, and the outer ring and the inner ring being arranged on the base plate,
 wherein at least two of the components are configured as separately producible components,
 wherein two of the separately producible components are connected by way of at least one of bonding, welding, riveting, clinching, clinch-bonding and rivet-bonding.

At least one embodiment of the invention further relates to a base body of a computed tomography drum, comprising:

at least two mutually independently producible sectors, the at least two mutually independently producible sectors being cast components, wherein the at least two mutually independently producible sectors are connected together to the base body.

At least one embodiment of the invention further relates to a base body of an embodiment, wherein two sectors, of the at least two mutually independently producible sectors, comprise interlocking subregions.

At least one embodiment of the invention further relates to a computed tomography drum, comprising:

the base body of an embodiment;

a fastening apparatus for an X-ray tube; and a fastening apparatus for an X-ray detector.

At least one embodiment of the invention further relates to a computed tomography device, comprising:

the computed tomography drum of an embodiment;

an X-ray tube;

an X-ray detector;

a drive to rotate the computed tomography drum; and a patient support.

BRIEF DESCRIPTION OF THE DRAWINGS

The above described properties, features and advantages of this invention are more clearly and distinctly described in the context of the following description making reference to the drawings. The drawings and descriptions do not restrict the invention and its embodiments in any way.

In different figures, the same components are provided with corresponding reference signs. The drawings are in general not to scale.

In the drawings:

FIG. 1 is a base body of a computed tomography drum according to the prior art,

Figure 2:
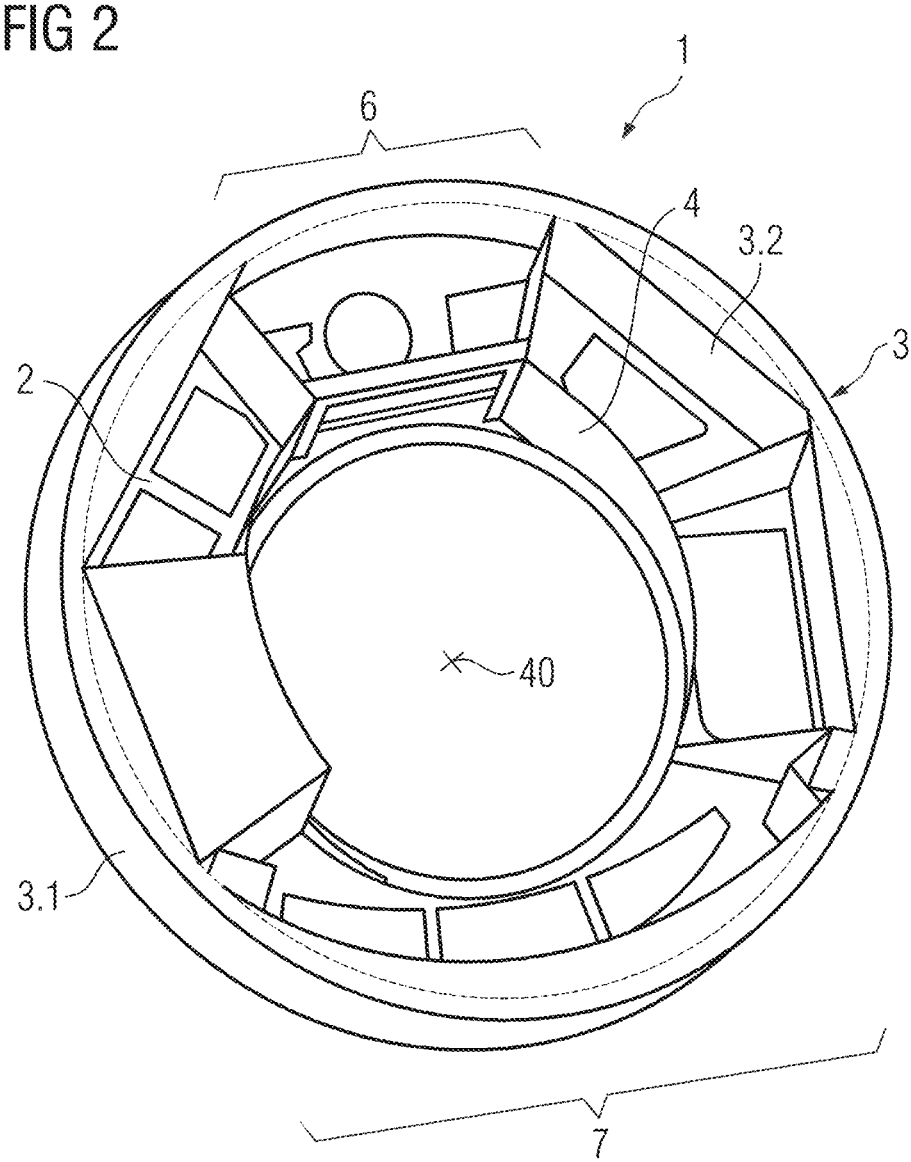
Figure 3:
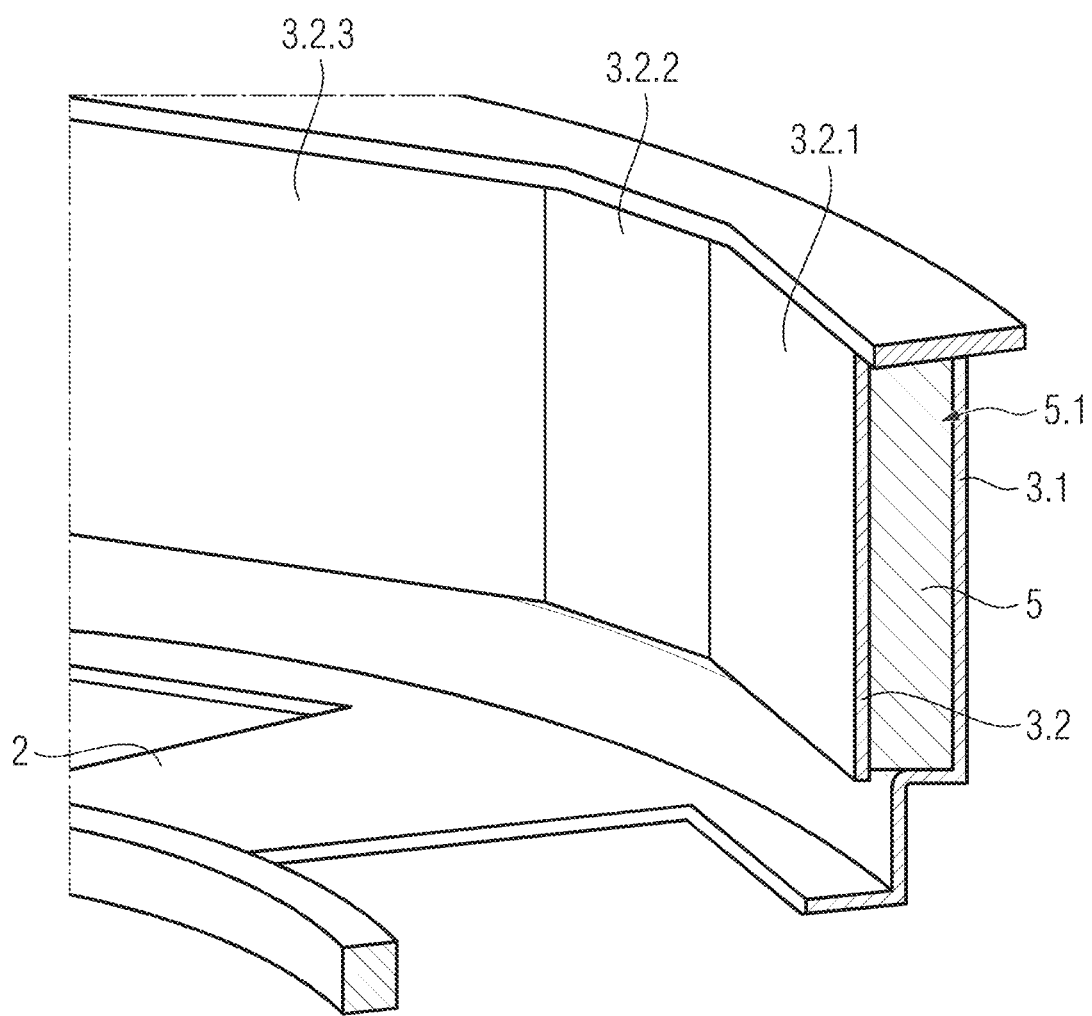
Figure 4:
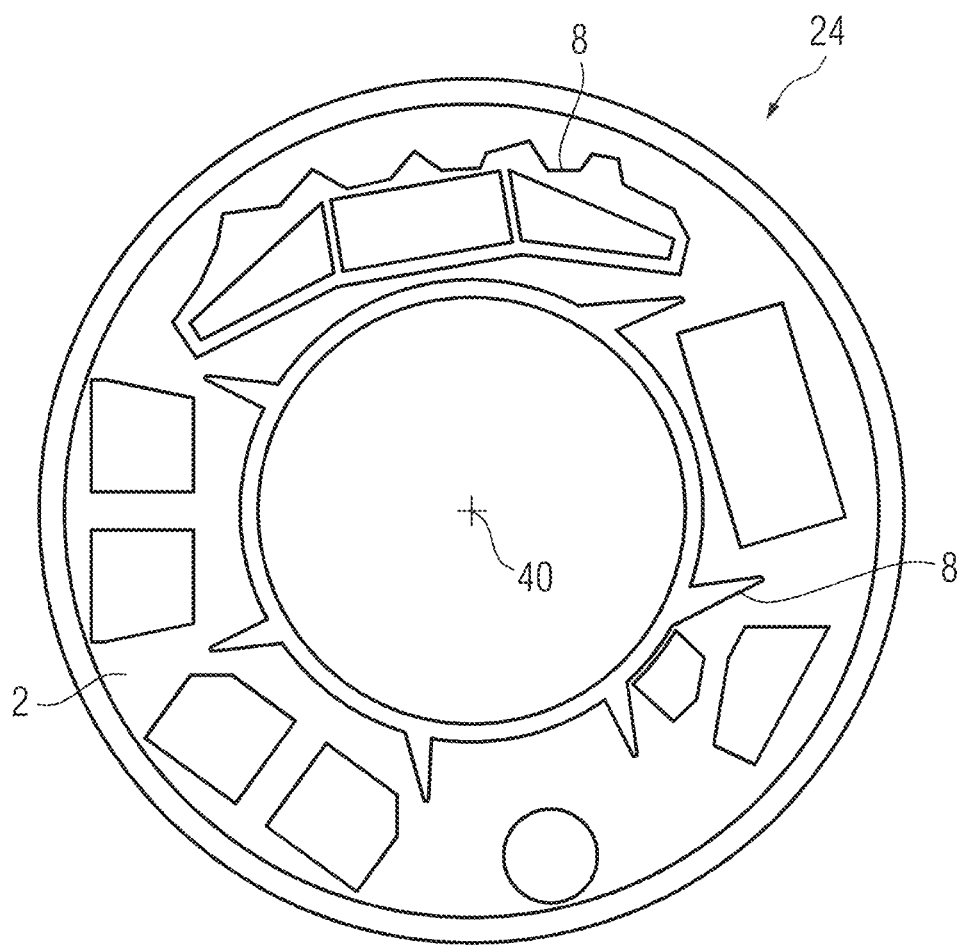
Figure 5:
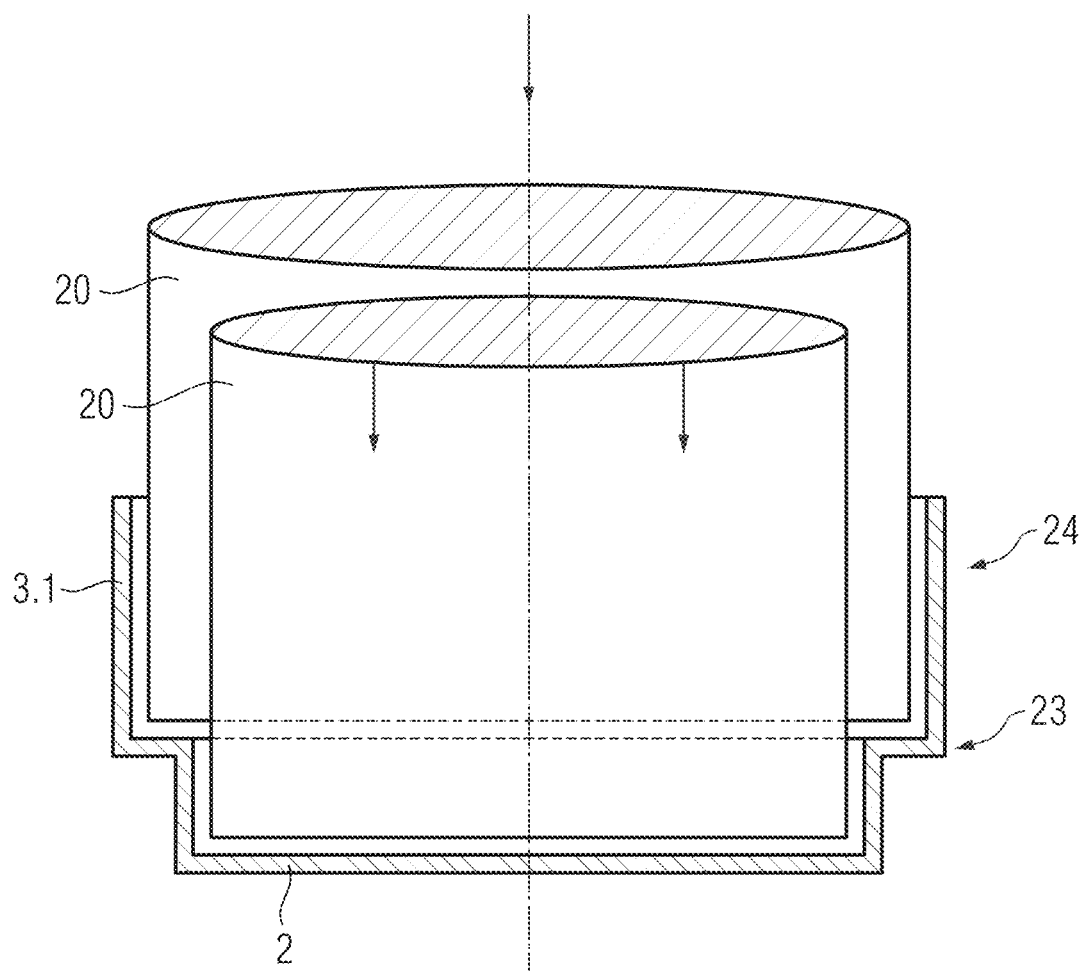
Figure 6:
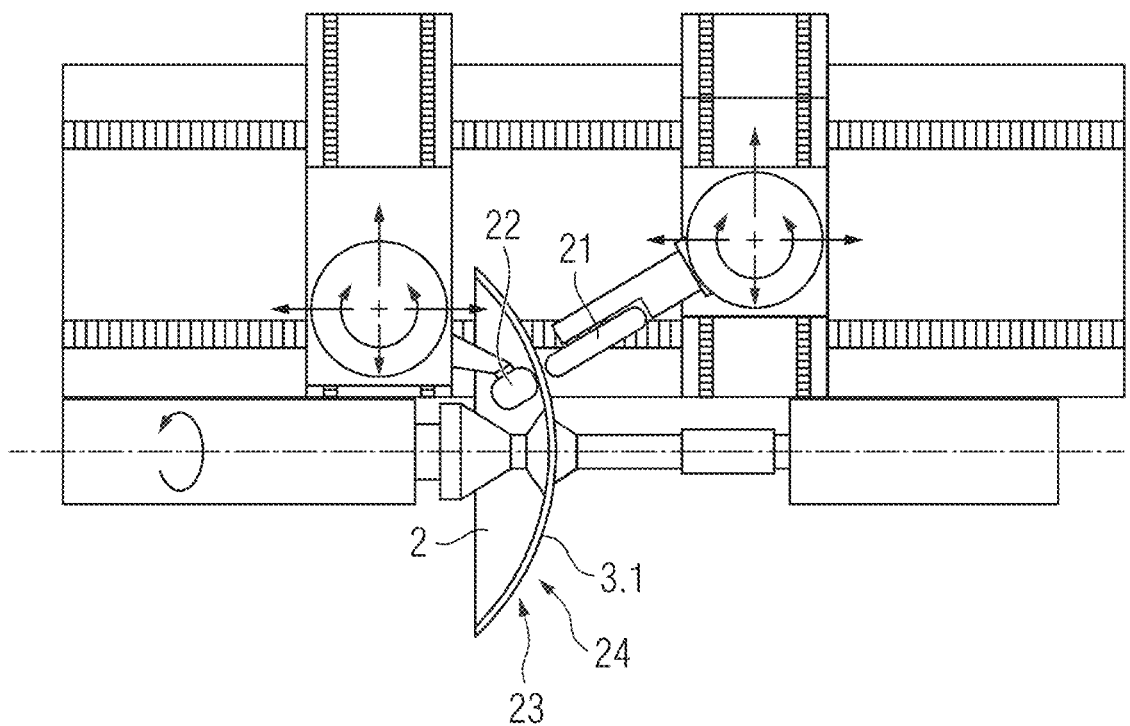
Figure 7:
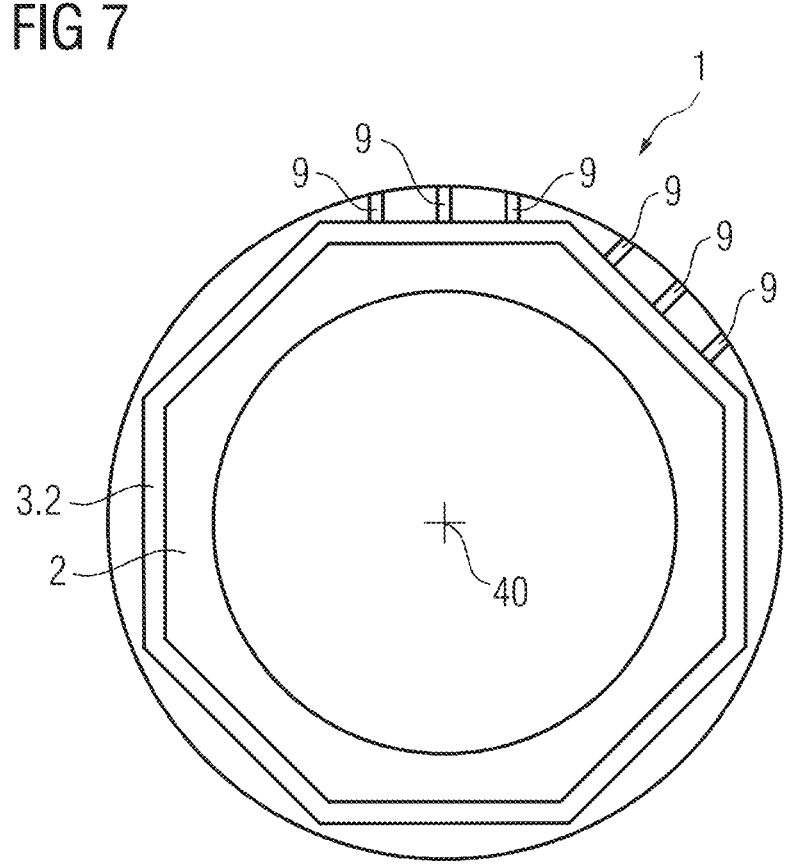
Figure 8:
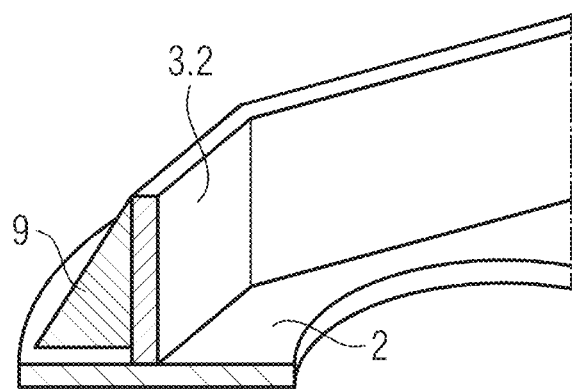
Figure 9:
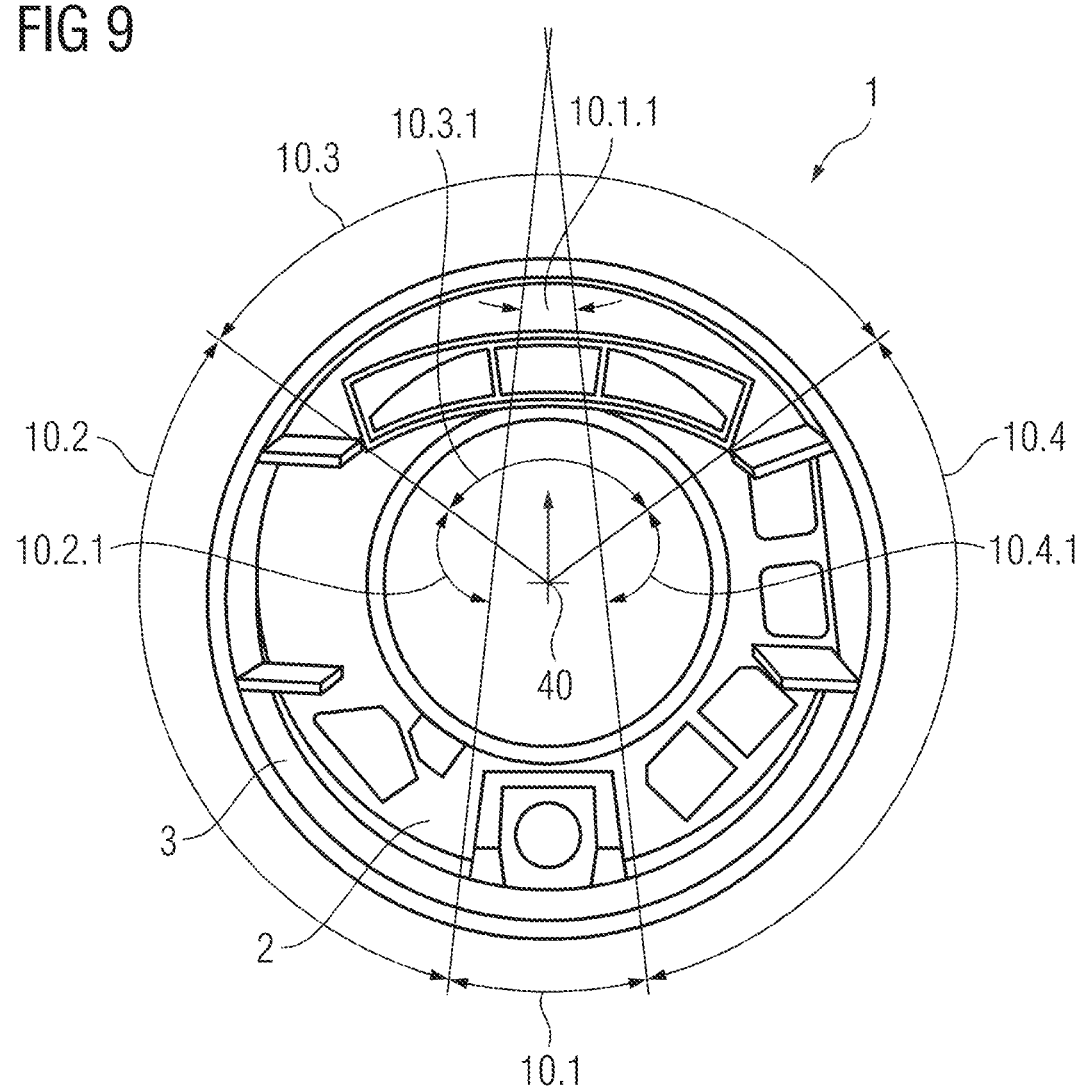
Figure 10:
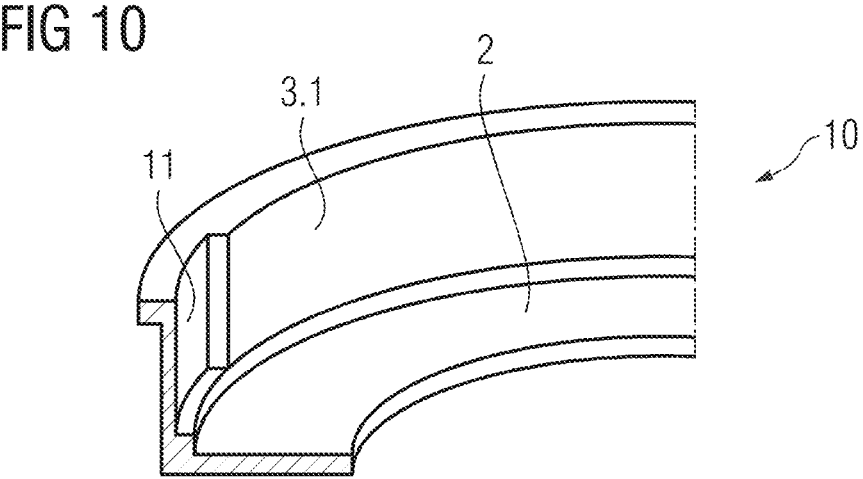
Figure 11:
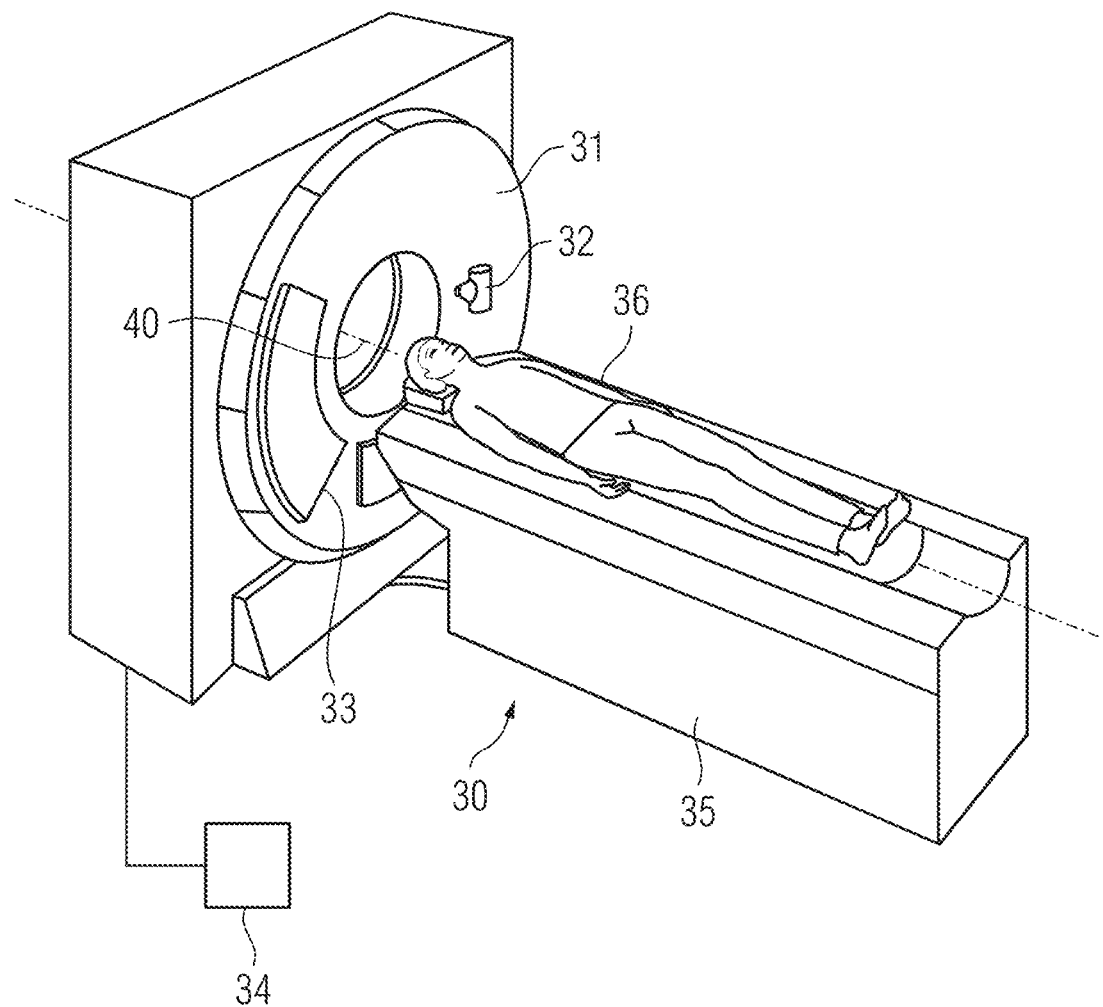

FIG. 2 is an example embodiment of a base body according to the invention of a computed tomography drum, comprising an inner ring with a height difference and an outer ring with an outer shell and at least one segment of a polygonal ring, FIG. 3 is a further example embodiment of a base body according to the invention of a computed tomography drum, comprising an outer ring with an outer shell and a polygonal ring which form an intermediate space, shown in a radial sectional representation, FIG. 4 is an example embodiment of a deep-drawn base plate of a base body according to the invention of a computed tomography drum, FIG. 5 is a production arrangement for deep-drawing a shell of a base body according to the invention of a computed tomography drum, FIG. 6 is a production arrangement for projection lengthening a shell of a base body according to the invention of a computed tomography drum, FIG. 7 is a further example embodiment of a base body according to the invention of a computed tomography drum, comprising a base plate, a polygonal ring and a plurality of stiffening elements, FIG. 8 is a representation of a radial cross-section of the example embodiment of FIG. 7, FIG. 9 is a further example embodiment of a base body of a computed tomography drum comprising four sectors, FIG. 10 is an example embodiment of a sector with an interlock, FIG. 11 is a computed tomography device.

DETAILED DESCRIPTION OF THE EXAMPLE EMBODIMENTS

The drawings are to be regarded as being schematic representations and elements illustrated in the drawings are not necessarily shown to scale. Rather, the various elements are represented such that their function and general purpose become apparent to a person skilled in the art. Any connection or coupling between functional blocks, devices, components, or other physical or functional units shown in the drawings or described herein may also be implemented by an indirect connection or coupling. A coupling between components may also be established over a wireless connection. Functional blocks may be implemented in hardware, firmware, software, or a combination thereof.

Various example embodiments will now be described more fully with reference to the accompanying drawings in which only some example embodiments are shown. Specific structural and functional details disclosed herein are merely representative for purposes of describing example embodiments. Example embodiments, however, may be embodied in various different forms, and should not be construed as being limited to only the illustrated embodiments. Rather, the illustrated embodiments are provided as examples so that this disclosure will be thorough and complete, and will fully convey the concepts of this disclosure to those skilled in the art. Accordingly, known processes, elements, and techniques, may not be described with respect to some example embodiments. Unless otherwise noted, like reference characters denote like elements throughout the attached drawings and written description, and thus descriptions will not be repeated. At least one embodiment of the present invention, however, may be embodied in many alternate forms and should not be construed as limited to only the example embodiments set forth herein.

It will be understood that, although the terms first, second, etc. may be used herein to describe various elements, components, regions, layers, and/or sections, these elements, components, regions, layers, and/or sections, should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items. The phrase "at least one of" has the same meaning as "and/or".

Spatially relative terms, such as "beneath," "below," "lower," "under," "above," "upper," and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below," "beneath," or "under," other elements or features would then be oriented "above" the other elements or features. Thus, the example terms "below" and "under" may encompass both an orientation of above and below. The device may be otherwise oriented (rotated 90 degrees or at other orientations) and the spatially relative descriptors used herein interpreted accordingly. In addition, when an element is referred to as being "between" two elements, the element may be the only element between the two elements, or one or more other intervening elements may be present.

Spatial and functional relationships between elements (for example, between modules) are described using various terms, including "connected," "engaged," "interfaced," and "coupled." Unless explicitly described as being "direct," when a relationship between first and second elements is described in the above disclosure, that relationship encompasses a direct relationship where no other intervening elements are present between the first and second elements, and also an indirect relationship where one or more intervening elements are present (either spatially or functionally) between the first and second elements. In contrast, when an element is referred to as being "directly" connected, engaged, interfaced, or coupled to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. Expressions such as "at least one of," when preceding a list of elements, modify the entire list of elements and do not modify the individual elements of the list. Also, the term "example" is intended to refer to an example or illustration.

When an element is referred to as being "on," "connected to," "coupled to," or "adjacent to," another element, the element may be directly on, connected to, coupled to, or adjacent to, the other element, or one or more other intervening elements may be present. In contrast, when an element is referred to as being "directly on," "directly connected to," "directly coupled to," or "immediately adjacent to," another element there are no intervening elements present.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

Before discussing example embodiments in more detail, it is noted that some example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order. Although the flowcharts describe the operations as sequential processes, many of the operations may be performed in parallel, concurrently or simultaneously. In addition, the order of operations may be re-arranged. The processes may be terminated when their operations are completed, but may also have additional steps not included in the figure. The processes may correspond to methods, functions, procedures, subroutines, subprograms, etc.

Specific structural and functional details disclosed herein are merely representative for purposes of describing example embodiments of the present invention. This invention may, however, be embodied in many alternate forms and should not be construed as limited to only the embodiments set forth herein.

Units and/or devices according to one or more example embodiments may be implemented using hardware, software, and/or a combination thereof. For example, hardware devices may be implemented using processing circuity such as, but not limited to, a processor, Central Processing Unit (CPU), a controller, an arithmetic logic unit (ALU), a digital signal processor, a microcomputer, a field programmable gate array (FPGA), a System-on-Chip (SoC), a programmable logic unit, a microprocessor, or any other device capable of responding to and executing instructions in a defined manner. Portions of the example embodiments and corresponding detailed description may be presented in terms of software, or algorithms and symbolic representations of operation on data bits within a computer memory. These descriptions and representations are the ones by which those of ordinary skill in the art effectively convey the substance of their work to others of ordinary skill in the art. An algorithm, as the term is used here, and as it is used generally, is conceived to be a self-consistent sequence of steps leading to a desired result. The steps are those requiring physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise, or as is apparent from the discussion, terms such as "processing" or "computing" or "calculating" or "determining" of "displaying" or the like, refer to the action and processes of a computer system, or similar electronic computing device/hardware, that manipulates and transforms data represented as physical, electronic quantities within the computer system's registers and memories into other data similarly represented as physical quantities within the computer system memories or registers or other such information storage, transmission or display devices.

In this application, including the definitions below, the term 'module' or the term 'controller' may be replaced with the term 'circuit.' The term 'module' may refer to, be part of, or include processor hardware (shared, dedicated, or group) that executes code and memory hardware (shared, dedicated, or group) that stores code executed by the processor hardware.

The module may include one or more interface circuits. In some examples, the interface circuits may include wired or wireless interfaces that are connected to a local area network (LAN), the Internet, a wide area network (WAN), or combinations thereof. The functionality of any given module of the present disclosure may be distributed among multiple modules that are connected via interface circuits. For example, multiple modules may allow load balancing. In a further example, a server (also known as remote, or cloud) module may accomplish some functionality on behalf of a client module.

Software may include a computer program, program code, instructions, or some combination thereof, for independently or collectively instructing or configuring a hardware device to operate as desired. The computer program and/or program code may include program or computer-readable instructions, software components, software modules, data files, data structures, and/or the like, capable of being implemented by one or more hardware devices, such as one or more of the hardware devices mentioned above. Examples of program code include both machine code produced by a compiler and higher level program code that is executed using an interpreter.

For example, when a hardware device is a computer processing device (e.g., a processor, Central Processing Unit (CPU), a controller, an arithmetic logic unit (ALU), a digital signal processor, a microcomputer, a microprocessor, etc.), the computer processing device may be configured to carry out program code by performing arithmetical, logical, and input/output operations, according to the program code. Once the program code is loaded into a computer processing device, the computer processing device may be programmed to perform the program code, thereby transforming the computer processing device into a special purpose computer processing device. In a more specific example, when the program code is loaded into a processor, the processor becomes programmed to perform the program code and operations corresponding thereto, thereby transforming the processor into a special purpose processor.

Software and/or data may be embodied permanently or temporarily in any type of machine, component, physical or virtual equipment, or computer storage medium or device, capable of providing instructions or data to, or being interpreted by, a hardware device. The software also may be distributed over network coupled computer systems so that the software is stored and executed in a distributed fashion. In particular, for example, software and data may be stored by one or more computer readable recording mediums, including the tangible or non-transitory computer-readable storage media discussed herein.

Even further, any of the disclosed methods may be embodied in the form of a program or software. The program or software may be stored on a non-transitory computer readable medium and is adapted to perform any one of the aforementioned methods when run on a computer device (a device including a processor). Thus, the non-transitory, tangible computer readable medium, is adapted to store information and is adapted to interact with a data processing facility or computer device to execute the program of any of the above mentioned embodiments and/or to perform the method of any of the above mentioned embodiments.

Example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order.

According to one or more example embodiments, computer processing devices may be described as including various functional units that perform various operations and/or functions to increase the clarity of the description. However, computer processing devices are not intended to be limited to these functional units. For example, in one or more example embodiments, the various operations and/or functions of the functional units may be performed by other ones of the functional units. Further, the computer processing devices may perform the operations and/or functions of the various functional units without sub-dividing the operations and/or functions of the computer processing units into these various functional units.

Units and/or devices according to one or more example embodiments may also include one or more storage devices. The one or more storage devices may be tangible or non-transitory computer-readable storage media, such as random access memory (RAM), read only memory (ROM), a permanent mass storage device (such as a disk drive), solid state (e.g., NAND flash) device, and/or any other like data storage mechanism capable of storing and recording data. The one or more storage devices may be configured to store computer programs, program code, instructions, or some combination thereof, for one or more operating systems and/or for implementing the example embodiments described herein. The computer programs, program code, instructions, or some combination thereof, may also be loaded from a separate computer readable storage medium into the one or more storage devices and/or one or more computer processing devices using a drive mechanism. Such separate computer readable storage medium may include a Universal Serial Bus (USB) flash drive, a memory stick, a Blu-ray/DVD/CD-ROM drive, a memory card, and/or other like computer readable storage media. The computer programs, program code, instructions, or some combination thereof, may be loaded into the one or more storage devices and/or the one or more computer processing devices from a remote data storage device via a network interface, rather than via a local computer readable storage medium. Additionally, the computer programs, program code, instructions, or some combination thereof, may be loaded into the one or more storage devices and/or the one or more processors from a remote computing system that is configured to transfer and/or distribute the computer programs, program code, instructions, or some combination thereof, over a network. The remote computing system may transfer and/or distribute the computer programs, program code, instructions, or some combination thereof, via a wired interface, an air interface, and/or any other like medium.

The one or more hardware devices, the one or more storage devices, and/or the computer programs, program code, instructions, or some combination thereof, may be specially designed and constructed for the purposes of the example embodiments, or they may be known devices that are altered and/or modified for the purposes of example embodiments.

A hardware device, such as a computer processing device, may run an operating system (OS) and one or more software applications that run on the OS. The computer processing device also may access, store, manipulate, process, and create data in response to execution of the software. For simplicity, one or more example embodiments may be exemplified as a computer processing device or processor; however, one skilled in the art will appreciate that a hardware device may include multiple processing elements or processors and multiple types of processing elements or processors. For example, a hardware device may include multiple processors or a processor and a controller. In addition, other processing configurations are possible, such as parallel processors.

The computer programs include processor-executable instructions that are stored on at least one non-transitory computer-readable medium (memory). The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc. As such, the one or more processors may be configured to execute the processor executable instructions.

The computer programs may include: (i) descriptive text to be parsed, such as HTML (hypertext markup language) or XML (extensible markup language), (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C#, Objective-C, Haskell, Go, SQL, R, Lisp, Java®, Fortran, Perl, Pascal, Curl, OCaml, Javascript®, HTML5, Ada, ASP (active server pages), PHP, Scala, Eiffel, Smalltalk, Erlang, Ruby, Flash®, Visual Basic®, Lua, and Python®.

Further, at least one embodiment of the invention relates to the non-transitory computer-readable storage medium including electronically readable control information (processor executable instructions) stored thereon, configured in such that when the storage medium is used in a controller of a device, at least one embodiment of the method may be carried out.

The computer readable medium or storage medium may be a built-in medium installed inside a computer device main body or a removable medium arranged so that it can be separated from the computer device main body. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The term code, as used above, may include software, firmware, and/or microcode, and may refer to programs, routines, functions, classes, data structures, and/or objects. Shared processor hardware encompasses a single microprocessor that executes some or all code from multiple modules. Group processor hardware encompasses a microprocessor that, in combination with additional microprocessors, executes some or all code from one or more modules. References to multiple microprocessors encompass multiple microprocessors on discrete dies, multiple microprocessors on a single die, multiple cores of a single microprocessor, multiple threads of a single microprocessor, or a combination of the above.

Shared memory hardware encompasses a single memory device that stores some or all code from multiple modules. Group memory hardware encompasses a memory device that, in combination with other memory devices, stores some or all code from one or more modules.

The term memory hardware is a subset of the term computer-readable medium. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The apparatuses and methods described in this application may be partially or fully implemented by a special purpose computer created by configuring a general purpose computer to execute one or more particular functions embodied in computer programs. The functional blocks and flowchart elements described above serve as software specifications, which can be translated into the computer programs by the routine work of a skilled technician or programmer.

Although described with reference to specific examples and drawings, modifications, additions and substitutions of example embodiments may be variously made according to the description by those of ordinary skill in the art. For example, the described techniques may be performed in an order different with that of the methods described, and/or components such as the described system, architecture, devices, circuit, and the like, may be connected or combined to be different from the above-described methods, or results may be appropriately achieved by other components or equivalents.

At least one embodiment of the invention relates to a base body of a computed tomography drum. The base body comprising: a base plate, an outer ring and an inner ring. The inner ring is arranged concentrically with the outer ring. The outer ring and the inner ring are arranged on the base plate. At least two of the components are configured as separately producible components. Two of the separately producible components are connected to one another by way of at least one of the following methods: bonding, welding, riveting, clinching, clinch-bonding and/or rivet-bonding.

The base body of the computed tomography (CT) drum forms, in particular, a ring shape. In other words, the base body is, in particular, annular. The base body is configured concentrically with a rotation axis and/or a rotation center. In a final arrangement of the base body in a computed tomography device, the rotation axis is typically oriented horizontally. In particular, the inner ring and the outer ring are arranged concentrically with the rotation axis.

The inner ring can be configured, in particular, annular and/or tubular and/or cylindrical. In particular, the inner ring can form a complete ring. Alternatively, the inner ring can form a part of a ring. Alternatively, the inner ring can form a cylinder of variable height. The outer ring can be configured, in particular, annular and/or tubular and/or cylindrical. In particular, the outer ring can form a complete ring. Alternatively, the outer ring can form a part of a ring.

The inner ring can have a smaller diameter than the outer ring. The inner ring therein encloses an opening of the base body round the rotation axis. The diameter of the inner ring is configured such that a patient on a patient support can be pushed into the opening of the base body. A typical diameter of the inner ring is 0.9 m. The outer ring encloses the base body radially outwardly. A typical diameter of the outer ring is 1.7 m.

The outer ring and the inner ring are arranged on the base plate. The base plate is arranged perpendicularly to the rotation axis. The base plate can be configured disk-shaped. In particular, the base plate can be formed circular. In other words, an outer edge of the base plate defines a circular form. In particular, a diameter of the base plate can correspond to the diameter of the outer ring. The base plate further comprises an opening and/or a hole. The opening is arranged in a center of the base plate. In other words, the opening of the base plate is arranged concentrically on the base plate. In particular, the opening of the base plate is formed circular. In particular, a diameter of the opening corresponds to the diameter of the inner ring and thus to a diameter of the opening of the base body. The inner ring is arranged on the base plate such that it finishes with the opening of the base plate, or substantially therewith. The outer ring is arranged on the base plate such that it finishes with the outer edge of the base plate, or substantially therewith.

In particular, at least two of the components are configured as separately producible components. In particular, the inner ring and the outer ring can be configured as separately producible components. In particular, the outer ring and the base plate can be configured as separately producible components. In particular, the inner ring and the base plate can be configured as separately producible components. In particular, the inner ring, the outer ring and the base plate can each be configured as separately producible components. In particular, a part and/or a component and/or a sub-component of a component can be configured to be separately producible. In this case, the component of which a part is separately producible is designated as separately producible.

The separately producible components are connected and/or joined to the base body of the CT drum. Therein, in particular, two components are always connected to one another. In particular, the outer ring is connected to the base plate. In other words, the outer ring is directly connected to the base plate. In particular, the inner ring is connected to the base plate. In other words, the inner ring is directly connected to the base plate. In particular, the inner ring and the outer ring are indirectly connected via the base plate.

For connecting, the components can, in particular, be bonded with an adhesive. In other words, the connection of the components is producible by bonding. In particular, the components can be bonded to one another under pressure. The bonding adhesive can be adapted to a material of the components to be connected. The bonding and/or bonding connection can be realized, for example, by way of one of the following reactions: a polyaddition reaction or a polycondensation reaction or a polymerization reaction. The selection of the adhesive takes place based upon the materials to be connected by way of the bonding. In other words, the adhesive can carry out one of the aforementioned reactions for bonding the components. Dependent upon the reaction, the adhesive has thermoplastic, elastomeric or thermosetting properties.

Alternatively or additionally, the components can be welded to one another to connect them. In other words, the connection of the components is producible by welding and/or fusing. In particular, the components can be connected by way of metal-active gas (MAG) welding. In particular, the MAG welding can be used when the components comprise and/or consist of structural steel. In particular, the welding can be carried out with a robot welding system.

Alternatively or additionally, the components can be riveted to one another for the connection. In other words, the connection of the components is producible by riveting or rivet-fastening. In other words, the components can be connected with at least one rivet. The rivet can be configured, for example, as a blind rivet or as a punch rivet. If the rivet is configured as a blind rivet, a through hole can be arranged at the location where the components are to be connected by the rivet. The blind rivet can then connect the components to one another through the through hole.

Alternatively or additionally, the components can be clinched for the connection. In other words, the connection of the components is producible by clinching. The process of clinching is also known as press-joining. In particular, the connection can be creatable by way of press-joining with a cutting portion and by way of press-joining without a cutting portion.

Alternatively or additionally, the connection of the components can be producible by clinch-bonding. For this, one of the variants of bonding described above and one of the variants of clinching described above are combined for connecting the components.

Alternatively or additionally, the connection of the components can be producible by rivet-bonding. For this purpose, one of the variants of riveting described above and one of the variants of clinching described above are combined for connecting the components.

The inventors have recognized that with the separately producible components, a design change of the base body is easily realizable. In particular, a design change for an individual, separately producible component can be easily realized, whereas the other components remain unchanged.

Furthermore, the inventors have recognized that the components are producible from any and different materials. The inventors have also recognized that the materials from which the components are made can be better adapted to mechanical conditions during a rotation of the base body. The inventors have also recognized that a bonding connection of the components is configured for connecting any, including different, materials. The inventors have also recognized that on a creation or production of a bonding connection and/or a rivet connection, no heating influence comes to bear upon the components. The inventors have also recognized that for the creation of a bonding connection, no costly machines are needed. The inventors have recognized that on a connection of the components by way of welding, a processing time and/or production time can be significantly reduced. The process time denotes a duration required for producing the base body. The inventors have recognized that the processing time can be reduced, in particular, by using a robot welding system.

The inventors have recognized that for the creation of a clinch connection, the components do not need to be prepared in any way. In other words, no pre-processing of the components to be connected is necessary in advance of the clinching. The inventors have recognized that in this way, the processing duration is reducible. The inventors have recognized that a combination of different methods and/or processes (bonding, welding, riveting, clinching) for creating the connection of two components combines the advantages of the methods.

According to one embodiments of the invention, at least one of the components consists of sheet metal.

In other words, at least one component can be produced and/or created from sheet metal. Therein, the sheet metal is typically very much larger in its width and length than in its thickness. The sheet metal typically has a thickness of between 1 mm and 20 mm. In particular, a production method of the at least one component is then based upon a sheet metal processing. In particular, all the components of the base body can consist of sheet metal.

The sheet metal can be, in particular, a rolled product made of metal. In particular, the sheet metal can be a sheet steel. In particular, the sheet metal can be formed from rolled steel. In particular, the rolled steel can be a rolled steel with the material designation S235J2C+N or S235JR.

In particular, the sheet metal can be protected against corrosion by a cathodic dip coating and/or by a wet paint coating and/or a powder paint coating.

The inventors have recognized that a component of the base body made of sheet metal is producible particularly flexibly. The inventors have recognized that a design change in a sheet metal processing is easily implementable. Furthermore, the inventors have recognized that sheet metal has advantageous mechanical properties on rotation of the base body. For example, the modulus of elasticity of sheet steel is approximately 210000 MPa, so that a deformation of the base body during the rotation can be reduced and/or minimized. In addition, the inventors have recognized that it is thus possible that the outer and/or inner ring can have a smaller wall thickness if it consists of sheet metal. In this way, a weight of the base body can be reduced.

In particular, due to the lower weight, the base body is rotatable about the rotation axis with a higher rotary speed. In other words, the lighter the base body is, the faster it can rotate about the rotation axis. The inventors have also recognized that sheet metal has advantageous properties with regard to its yield strength, its tensile strength and its elongation at failure. In particular, the base body made of sheet metal has a constant deformation during rotation with a small wall thickness and thus a very good fundamental rigidity. The inventors have also recognized that, as compared with aluminum-silicon casting alloy, sheet metal results in a reduction in the material costs. The inventors have also recognized that during sheet metal processing, no or hardly any postprocessing of the base body is needed. In particular, metal cutting postprocessing can be dispensed with. The inventors have thus recognized that the production process of the base body can be fully automated since manual postprocessing can be dispensed with.

According to a further embodiment of the invention, the outer ring comprises an outer shell and at least one segment of a polygonal ring. Therein the outer shell and the at least one segment of the polygonal ring are configured to be separately producible.

In particular, the outer ring comprises an annular or tubular or cylindrical outer shell. A height of the outer shell defines the height of the cylinder which forms the outer shell.

The polygonal ring encloses, in particular, a base area of a polygon. The polygon can be, in particular, a triangle, a rectangle or a pentagon or a hexagon or a heptagon or an octagon. The polygonal ring thus comprises a plurality of side edges. The number of side edges corresponds to the number of corners of the polygon. In each case, two side edges are arranged at an angle to one another in extension of one another. All the side edges together form a closed combination. In other words, the first side edge is arranged on the second side edge, the second side edge is arranged on the third side edge and the last side edge is again arranged on the first side edge. In particular, all the side edges can be equally sized. Alternatively, at least two side edges can be differently sized. The side edges can form a height of the polygonal ring perpendicularly to the area enclosed by them. In other words, the polygonal ring can encompass a height.

In particular, the height of the polygonal ring can correspond to the height of the outer shell. A diameter of the polygonal ring can be given by a diameter of a circle enclosing the polygonal ring. The diameter of the polygonal ring can be, in particular, smaller than or equal to a diameter of the outer shell.

A segment of a polygonal ring corresponds to a side edge of the polygonal ring. In particular, the outer ring can comprise only one segment and/or only one side edge of the polygonal ring. In particular, the outer ring can comprise as many segments and/or side edges of the polygonal ring as desired.

The at least one segment of the polygonal ring and the outer shell are configured to be separately producible. In particular, the at least one segment of the polygonal ring and the outer shell consist of different materials. Alternatively, the at least one segment of the polygonal ring and the outer shell consist of the same material. In particular, the at least one segment of the polygonal ring and/or the outer shell consist of sheet metal.

In particular, the at least one segment of the polygonal ring can be directly connected to the outer shell. Alternatively, the at least one segment of the polygonal ring and the outer shell can be connected to one another indirectly via the base plate.

The inventors have recognized that the outer ring is producible more flexibly if the outer shell and the at least one segment of the polygonal ring are producible separately. In addition, the inventors have recognized that in this way, a weight of the outer ring can be reduced since an intermediate space and/or hollow space between the outer shell and the at least one segment of the polygonal ring can be unfilled or filled with any desired, in particular, light material.

According to a further embodiment of the invention, the at least one segment of the polygonal ring is arranged concentrically in the outer shell.

The at least one segment of the polygonal ring is arranged concentrically in the outer shell, in particular, if a polygonal ring comprising the at least one segment is arranged concentrically in the outer shell. In other words, the at least one segment is then arranged as if it were arranged in a concentric polygonal ring arranged concentrically with the outer shell.

The inventors have recognized that the at least one segment should be arranged, for stability reasons during rotation, concentrically in the outer shell. The inventors have recognized that then the at least one segment rotates with a constant spacing from the rotation axis on rotation of the base body. The inventors have recognized that, in this way, an imbalance of the base body can be prevented.

According to a further embodiment of the invention, the outer shell and/or the at least one segment of the polygonal ring is connected to the base plate.

The connection can be configured as described above. In other words, the connection of the outer shell and/or of the at least one segment to the base plate is producible by bonding and/or welding and/or riveting and/or clinching and/or clinch-bonding and/or clinch/riveting. These methods for producing the connection can be configured in the variants described above.

If the outer shell and the at least one segment of the polygonal ring are each connected to the base plate, the outer shell and the at least one segment of the polygonal ring are at least indirectly connected to one another. In particular, a direct connection between the outer shell and the at least one segment of the polygonal ring are not necessary. Alternatively, the outer shell and the at least one segment of the polygonal ring can be directly connected to one another.

In particular, it is sufficient if on a direct connection of the outer shell and of the at least one segment of the polygonal ring, only either the outer shell or the at least one segment of the polygonal ring is directly connected to the base plate. In particular, the outer shell and the at least one segment of the polygonal ring are connected to one another at least at one corner of the polygonal ring. In other words, the segment and/or the side edge can be connected at a side of the side edge to the outer shell, wherein the side of the side edge defines the height of the segment and/or the polygonal ring. Alternatively or additionally, the outer shell and the at least one segment of the polygonal ring can be connected to one another by way of a web. Alternatively or additionally, the outer shell and the at least one segment of the polygonal ring can be connected to one another by way of a filler material or a material in the intermediate space between the outer shell and the segment.

The inventors have recognized that for the stability of the base body, at least the outer shell and/or the at least one segment of the polygonal ring is connected to the base plate.

According to a further embodiment of the invention, an intermediate space between the at least one segment of the polygonal ring and the outer shell comprises a matrix.

In particular, the intermediate space is formed by a hollow space between the outer shell and the at least one segment of the polygonal ring. In particular, a volume of the intermediate space is dependent upon the difference of the diameter of the polygonal ring and the outer shell, on the number of corners of the polygonal ring, on the height of the outer shell and the polygonal ring and on the number of segments that the outer ring comprises.

The matrix can be configured, in particular, as a sandwich structure. In particular, the matrix can be configured as an aluminum honeycomb structure in a plastics matrix. In some embodiments, the matrix can be realized with any desired pressure-resistant structures with a low density (honeycomb structure) or materials (foams).

The inventors have recognized that a filling of the intermediate space with a matrix enhances or increases the stability of the base body. In addition, the inventors have recognized that the weight of the base body can be reduced in comparison with the cast component or cast part by introducing the matrix. In particular, by way of the lower weight, wear due to the rotation of the base body can be reduced. In addition, more economical components can be used for driving the rotation of the base body.

According to a further embodiment of the invention, the base plate can be made from a round blank.

In particular, the base plate is made from a sheet metal round blank. The round blank herein has a round shape. In particular, the shape of the round blank is disk-shaped or circular. The sheet metal round blank consists of a round or circular metal sheet.

The base plate is producible, in particular, by deep-drawing from the round blank. The base plate can be deep-drawn from the round blank in one or more steps. The base plate can be deep-drawn from a round blank, in particular, by pressing with one or more punches.

In particular, the base plate can comprise at least one deep-drawn depression and/or elevation in order to provide an interlocking connection to at least one separately producible component. In other words, at least one depression and/or elevation can be deep-drawn into the base plate, facilitating a positioning of the inner ring and/or of the outer ring and/or of the outer shell and/or of the at least one segment of the polygonal ring. In particular, a depression which is formed for fastening the X-ray tube and/or the X-ray detector can be deep-drawn in the base plate.

The inventors have recognized that the base plate is simply producible from a round blank. The inventors have also recognized that no subsequent processing of the surface of the base plate is necessary if the base plate has been made from a round blank. The inventors have also recognized that the deep-drawing enables a flexible production of the base plate. In other words, a flexible adaptation to a design change of the base plate is possible. The inventors have also recognized that the base plate undergoes strain-hardening due to the deep-drawing and therefore the stability of the base plate can be increased.

According to a further embodiment of the invention, beads are worked into the base plate by pressing and/or placement of a rolled-in sheet metal.

In particular, the beads can be worked in by pressing on a punch or by rolling a punch into the base plate. In other words, the beads can be worked into the base plate by deep-drawing.

Alternatively or additionally, the beads can be worked into the base plate by placement of a rolled-in sheet metal on the base plate. In particular, the rolled-in sheet metal can be connected to the base plate by way of one of the processes described above. The rolled-in sheet metal can be processed by deep-drawing and/or rolling such that it forms a stabilizing structure.

The inventors have recognized that the beads additionally stabilize the base plate. The inventors have recognized that the beads stabilize the base plate in such a way that the base plate can be produced from a thinner sheet metal. The inventors have recognized that thereby a cost-saving in the material costs and a weight saving in the base body can be achieved. The inventors have also recognized that the beads can be worked into the base plate during the process of deep-drawing the base plate.

According to a further embodiment of the invention, the outer shell and the base plate form a shell of the base body. Therein, the shell is producible by deep-drawing a round blank.

The round blank can be, in particular, a sheet metal round blank. The round blank can be configured as described above.

The base plate and the outer shell form, in particular, a common component, the shell. The shell is producible from the round blank by deep-drawing. The shell is configured, in particular, basin-shaped. The shell comprises, in particular, the circular base plate and the cylindrical outer shell arranged on the base plate. The opening of the base plate can subsequently be stamped or sawn out of the shell, etc., after the deep-drawing. The opening is therein stamped or sawn out of the base plate concentrically with the outer shell and the base plate.

The shell can be deep-drawn out of the round blank, in particular, in one or more steps. The round blank can have a thickness which gives the shell sufficient stability during a rotation of the base body.

In particular, the inner ring and/or the at least one segment of the polygonal ring can be inserted into and/or connected to the shell concentrically.

The inventors have recognized that, due to the deep-drawing, the shell undergoes an additional strain-hardening. The stability of the base body is thereby increased. The inventors have also recognized that the shell producible by deep-drawing is flexibly adaptable to the design change. In addition, the inventors have recognized that the shell can be configured stable due to the deep-drawing such that the outer ring can comprise just one segment or an incomplete polygonal ring without loss of stability.

According to a further embodiment of the invention, the outer shell and the base plate form a shell of the base body. The shell is thereby producible from a round blank by a projection lengthening process.

The shell can be configured as described above. The round blank can be configured as described above.

The projection lengthening process is described, for example, in the book Fertigungsverfahren [Manufacturing Processes] 4—Umformen [Forming], 2017, Springer Verlag, by Fritz Klocke. In the projection lengthening process, an edge of the round blank is bent with a pressure roller and a counterroller to an inner region of the round blank. The inner region of the round blank is enclosed, in particular, by the edge or edge region of the round blank. In other words, the edge can form a circular ring round the interior region of the round blank. A radial extent of the edge of the round blank can be dependent upon the height of the outer shell. In particular, the edge is bent perpendicularly to the inner region of the round blank. In particular, the edge of the round blank forms the outer shell. In particular, the inner region of the round blank forms the base plate.

In particular, the inner ring and/or the at least one segment of the polygonal ring can be inserted into and/or connected to the shell concentrically.

The inventors have recognized that, due also to the projection lengthening process, the shell undergoes a strain-hardening which increases the stability of the base body. The inventors have recognized that the shell producible with the projection lengthening process is flexibly and rapidly adaptable to a design change. In addition, the inventors have recognized that the shell can be configured stable due to the projection lengthening process such that the outer ring can comprise just one segment or an incomplete polygonal ring without loss of stability.

According to a further embodiment of the invention, the base body forms a subregion between the outer ring and the inner ring, in each case, for accommodating an X-ray tube and an X-ray detector. A height of the inner ring in the subregion in which the X-ray tube is arranged and a height of the inner ring in a subregion in which the X-ray detector is arranged have a height difference.

The X-ray tube is advantageously a rotating anode X-ray tube. Alternatively, the X-ray source can also be a transmission anode X-ray tube.

In a preferred embodiment, the X-ray detector is a pixelated X-ray detector or detector. This can relate to a semiconductor detector or a scintillator detector. In a preferred embodiment, the X-ray detector is a digital X-ray detector.

The subregion in which the X-ray tube can be located can be located in the base body opposite the subregion in which the X-ray detector can be arranged. In other words, the rotation axis lies on the shortest connection between the X-ray tube and the X-ray detector.

In particular, the subregions can be formed, for example, by elevations or depressions in the base plate. Alternatively or additionally, a segment of the polygonal ring can be arranged in each subregion.

In particular, the inner ring is arranged concentrically with the outer ring on the base plate. In particular, the X-ray tube and the X-ray detector can be arranged between the outer ring and the inner ring. In particular, the X-ray tube can be arranged on and/or fastened to the outer ring and/or to the base plate and/or to the inner ring. In particular, the X-ray detector can be arranged on and/or fastened to the outer ring and/or to the base plate and/or to the inner ring. In particular, the X-ray tube and the X-ray detector can be releasably or non-releasably fastened. In particular, for fastening, the X-ray tube or the X-ray detector can be screwed, riveted, soldered, welded, etc.

In particular, a simulation can be carried out for optimizing a topology of the base body. In particular, the simulation shows that on a rotation of the base body on the subregion in which the X-ray tube is arranged, greater centrifugal forces act than in other regions of the base body. In particular, for stabilization, the inner ring in the subregion of the X-ray tube, can be constructed higher than in the subregion of the X-ray detector. The height of the inner ring is given perpendicularly to the base plate. Typically, the inner ring has a maximum height of approximately 0.4 m and a minimum height of 0.2 m. In particular, the inner ring thus has a height difference between the two subregions. In particular, the height of the inner ring can decline continuously from the subregion of the X-ray tube to the subregion of the X-ray detector. Alternatively, the height can decline step-wise in one or more steps. In other words, the height difference can be bridged continuously or step-wise. In particular, the inner ring is thus configured optimized for topology.

The inventors have recognized that by way of the topology optimization of the inner ring, the material costs and the weight of the base body can be reduced. The inventors have also recognized that therein, no sacrifices have to be made with regard to the stability on rotation of the base body. The stability defines, in particular, the deformation of the base body during rotation.

According to an alternative embodiment of the invention, the inner ring and/or the outer ring can be formed by an interrupted structure. In an interrupted structure, the inner ring and/or the outer ring does not form a complete, closed ring, but comprises merely at least a subregion of the corresponding ring. In particular, the inner ring and/or the outer ring can comprise only the at least one subregion that is necessary for the stability.

The inventors have recognized that in this way, it is possible to reduce the weight of the base body.

According to a further embodiment of the invention, the outer ring comprises a polygonal ring and a plurality of stiffening elements. The plurality of stiffening elements supports the polygonal ring against the base plate.

The base plate can be configured as described above. In particular, the base plate is producible by way of deep-drawing. The inner ring can be configured as described above. In particular, the inner ring can be configured optimized for topology. In particular, the polygonal ring can be configured as described above. In particular, in this embodiment, the outer ring comprises the complete polygonal ring. In other words, in this embodiment, the outer ring comprises all the segments of the polygonal ring.

In particular, the polygonal ring is connected to the base plate. In particular, the connection can be configured as described above. In particular, the stiffening elements are configured as a separate component. The stiffening elements can be configured as angles. In particular, the stiffening elements can have a right angle if the polygonal ring is arranged perpendicularly to the base plate. In particular, each segment of the polygonal ring can be supported against the base plate with at least one stiffening element. In particular, for this purpose, the stiffening elements can be arranged perpendicularly to the base plate. In particular, each segment of the polygonal ring can be supported against the base plate with more than one stiffening element. In particular, each stiffening element can be arranged perpendicularly to the corresponding segment of the polygonal ring to be supported and to the base plate. In particular, a stiffening element can be connected to the base plate and the corresponding segment of the polygonal ring. In particular, the connection can be configured as described above. In other words, the connection can be provided by bonding and/or welding and/or riveting and/or clinching and/or clinch-bonding and/or clinch/riveting. In particular, the stiffening elements can be arranged radially outwardly from the polygonal ring. Alternatively, the stiffening elements can be arranged radially inwardly from the polygonal ring.

The inventors have recognized that by way of the stiffening elements, the outer shell can be dispensed with. The inventors have recognized that this leads to a reduced complexity of the shape of the base body. In particular, adaptations to the design change can be easily implemented. The inventors have recognized that by way of the stiffening elements, the material costs and the weight of the base body can be reduced.

At least one embodiment of the invention further relates to a base body of a computed tomography drum, the base body comprising at least two mutually independently producible sectors. Therein, the sectors are cast components. Therein, the sectors are connected together to the base body.

The computed tomography drum and the base body can be configured as described above. An outer form of the base body can take the shape, in particular, of a cylinder. In particular, the outer shape of the base body forms a hollow cylinder. The outer shape defines the smallest geometrical form which the base body can comprise and/or encompass.

In particular, as described above, the base body can comprise a base plate, an outer ring and an inner ring. The inner ring can be configured, in particular, optimized for topology as described above. The base plate therein denotes the circular base surface of the cylinder or hollow cylinder.

The base plate can be subdivided, in particular, into at least two sectors or circular sectors. In other words, the base plate can comprise at least two sectors. In particular, the outer ring and/or the inner ring are then also subdivided into corresponding sectors. A sector of the outer ring and/or the inner ring therein comprises an angular region of the outer ring and/or the inner ring corresponding to the sector. In particular, a sector of the outer ring and a corresponding sector of the inner ring is configured with the corresponding sector of the base plate as a cast component. In particular, therefore, the base body is subdivided or partitioned into at least two sectors. In other words, the base body comprises at least two sectors. In particular, therefore, each of the sectors comprises a sector of the base plate, a sector of the outer ring and a sector of the inner ring in a cast component. In alternative embodiments, the inner ring can be configured as a separate component as described above. Then, a sector of the base body comprises a sector of the base plate and a sector of the outer ring. In particular, the base body can comprise two, three, four, five or six sectors. A sector can be denoted by its opening angle. The opening angle of the sectors that are included by the base body can be the same for all sectors in some embodiments. In alternative embodiments, the opening angle of at least two sectors can be different.

In particular, each of the sectors can be configured as a cast component. The sectors can each be cast, in particular, from an aluminum-silicon casting alloy. Therein, the casting alloy is molded for casting a sector in a corresponding mold. In particular, a diecasting process or a permanent mold casting process can be used. Alternatively, the sand casting process can be used for casting the sectors.

The inventors have recognized that by subdividing the base body into sectors, a design change can be adopted more easily since, rather than the mold of the entire cast body, only the mold of the sector to be changed must be adapted. The inventors have also recognized that, due to the smaller cast components or cast parts, smaller tolerances can be achieved than if the entire base body is configured as a cast component or cast part. A smaller reworking effort is therefore needed than for a base body made of a single cast component or cast part. The inventors have recognized that due to their smaller size in comparison with the entire base body, the cast components can be cast or produced with the sand casting process, a diecasting process or a permanent mold casting process. By this, a remachining of a surface of the cast components can be dispensed with. In particular, therefore, no or hardly any remachining of the cast components is necessary. The inventors have recognized that both the above described disadvantages of the remachining can thus be prevented. The inventors have also recognized that the production process of the base body can be fully automated since manual postprocessing can be dispensed with.

According to a possible embodiment of the invention, a subregion of the base body is configured for accommodating an X-ray tube and an X-ray detector in each case. Therein, the subregions are each included by separately producible sectors.

In particular, the base body can be configured to accommodate an X-ray tube in a subregion of the base body and, in a further subregion, an X-ray detector. In other words, the X-ray tube can be arranged in a first subregion in the base body and the X-ray detector can be arranged in a second subregion. The X-ray tube and the X-ray detector can be configured as described above. In particular, the subregion which is configured for accommodating the X-ray tube can be included by a first sector. In particular, the subregion which is configured for accommodating the X-ray detector can be included by a second sector. In particular, the first and the second sector can be configured as separately producible sectors. In other words, the subregions are each included by a separately producible sector of the base body. In other words, the base body can be subdivided into individual sectors according to structural considerations. Structural considerations can be, in particular, possible arrangements of imaging components for computed tomography imaging within particular sectors. Alternatively or additionally, structural considerations can be other mechanical requirements in a particular sector of the base body. Alternatively or additionally, a structural consideration can be, for example, that a corresponding sector forms a cable duct and/or a holder for a data transfer unit and/or a holder for a computer unit, etc.

The inventors have recognized that a structural subdivision of the base body into individual sectors, wherein the individual sectors are configured as individual cast components or cast parts, allows an adaptation or adoption of design changes particularly effectively. Furthermore, the inventors have recognized that on a structural subdivision of the base body into individual sectors, the sectors can be adapted, for example, in respect of a mechanical property, etc. For example, it is possible to optimize individual sectors in respect of their wall thickness and/or the material.

According to a further embodiment of the invention, two sectors comprise interlocking subregions, in each case.

In particular, the interlocking subregions are configured such that, in each case, two sectors which, placed on one another or assembled, form at least one part of the base body, can be placed on one another or assembled interlockingly or flush with one another. In particular, the interlocking subregions can be configured such that the corresponding two sectors can be placed on one another flush and stably. In particular, for this purpose, each of the two sectors comprises a part of the interlock. In particular, for this purpose, one of the sectors can form a groove and/or a nose. In particular, the other one of the two sectors can form a depression which is formed to be interlocking with the groove. Alternatively, the interlock can be formed by exactly fitting threads on the two sectors. In particular, in this way the at least two sectors can be assembled or combined to form the base body in an interlocking manner.

In particular, the interlocking subregion of a sector is arranged on the edge of the sector which has been connected to a corresponding edge of the other sector. In particular, each sector is connected to another sector at two edges. In particular, in some embodiments, on both edges the other sector can be the same sector if the base body comprises only two sectors. Alternatively, the sector can be connected at each of the two edges to different other sectors. In particular, the sector can comprise or form an interlocking subregion at each of the two edges, each subregion being formed to be compatible with an interlocking subregion of the corresponding other sector.

The inventors have recognized that, by way of an interlock, a correct assembly of the sectors to the base body can be ensured. In other words, the inventors have recognized that by way of the interlock of the two sectors, it can be prevented that the sectors are placed on one another displaced relative to one another when the base body is assembled.

According to a further possible embodiment of the invention, the at least two sectors are connected to one another with a hybrid joining process.

The hybrid joining process can combine at least two of the methods described above for connecting two components. In particular, the hybrid joining process can comprise a combination of riveting and bonding.

The inventors have recognized that with the hybrid joining process, the sectors can also be stably connected to one another on a rotation of the base body. Furthermore, the inventors have recognized that with the hybrid joining process, different materials can be connected to one another.

At least one embodiment of the invention further relates to a computed tomography drum which comprises a base body, a fastening apparatus for an X-ray tube and a fastening apparatus for an X-ray detector.

The base body can be configured according to one of the embodiments described above. The X-ray tube and the X-ray detector can be configured as described above.

The fastening apparatus can comprise, for example, a thread for screw-fastening the X-ray tube and/or the X-ray detector. Alternatively, the fastening apparatus can be a support surface on which the X-ray tube and/or the X-ray detector can be welded and/or bonded and/or riveted.

At least one embodiment of the invention further relates to a computed tomography device comprising a computed tomography drum, an X-ray tube, an X-ray detector, a drive for a rotation of the computed tomography drum and a patient support.

The computed tomography drum, the X-ray tube and the X-ray detector can be configured as described above. The drive is configured to rotate the computed tomography drum about the rotation axis described above. The patient support is configured to position a patient in the rotation axis of the computed tomography drum. The patient support can, in particular, be configured movable. In addition, the patient support can be configured height-adjustable.

Figure 1:
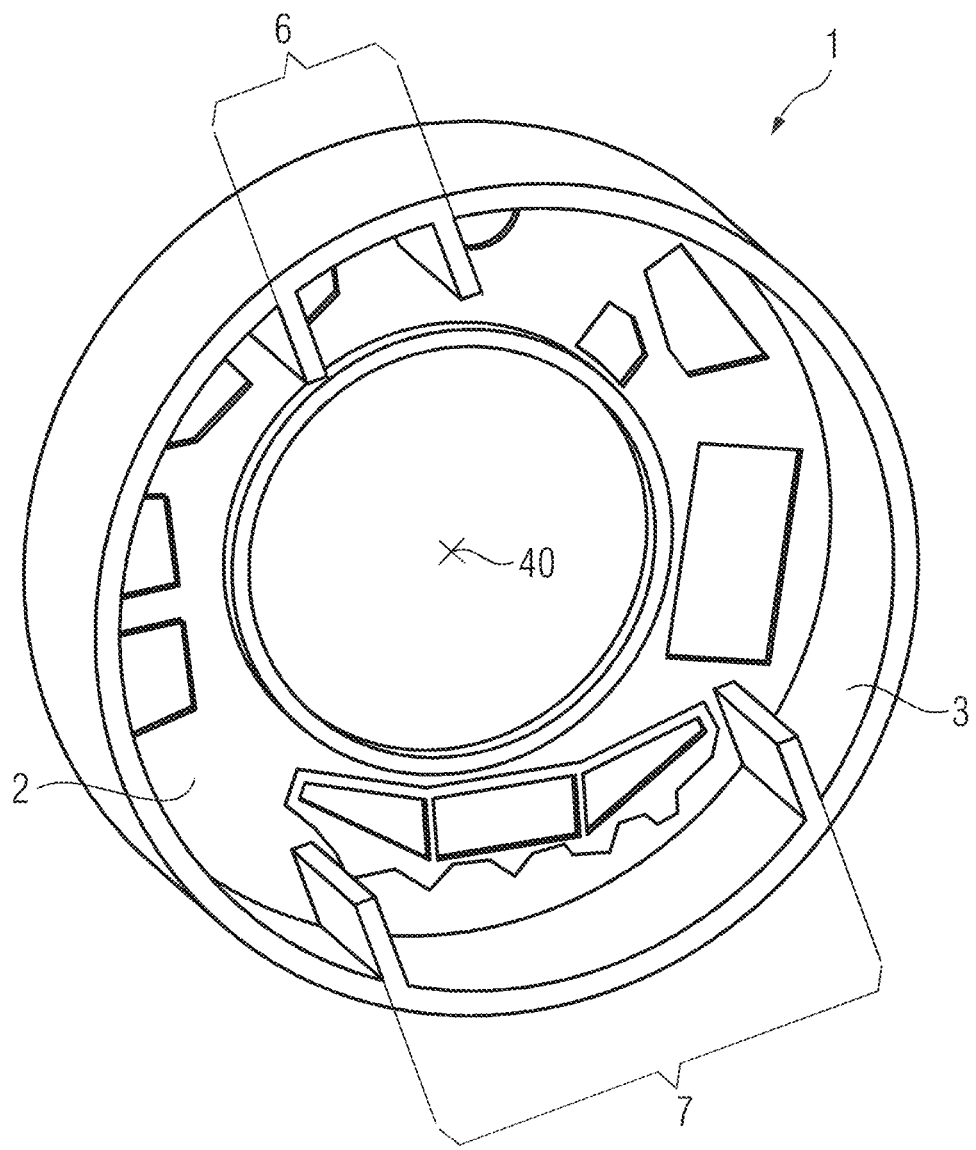

FIG. 1 shows a base body 1 of a computed tomography drum 31, according to the prior art.

The base body 1 is produced by way of a casting process. The casting process can comprise a sand casting process. The base body 1 consists of a single cast component or cast part. The base body 1 comprises a base plate 2, an outer ring 3 and an inner ring 4. For the sake of clarity, the inner ring 4 is not shown in the representation. The base plate 2 comprises a circular or annular surface. In other words, the base plate 2 comprises a circular surface with a central opening. The opening is arranged concentrically on the base plate 2. The opening is arranged symmetrically in relation to a rotation axis 40. The rotation axis 40 extends through a midpoint or a center of the base plate 2.

The outer ring 3 is arranged concentrically on the base plate 2. The outer ring 3 is formed cylindrically. The outer ring 3 terminates with an outer edge of the base plate 2. In other words, a diameter of the outer ring 3 corresponds to a diameter of the base plate 2. The inner ring 4 is, in particular, also configured cylindrical. The inner ring 4 is arranged concentrically on the base plate 2. A diameter of the inner ring 4 corresponds to a diameter of the opening of the base plate 2.

The base body 1 comprises a subregion 6, which is configured for the accommodation of an X-ray tube 32. The base body 1 also comprises a subregion 7, which is configured for the accommodation of an X-ray detector 33. The two subregions 6, 7 are arranged in the base body 1 opposite one another.

FIG. 2 shows an example embodiment of a base body 1 of a computed tomography drum 31 according to the invention, comprising an inner ring 4 with a height difference and an outer ring 3 with an outer shell 3.1 and a polygonal ring 3.2.

The base body 1 also comprises a base plate 2. In the example embodiment, the base plate 2, the outer shell 3.1, the polygonal ring 3.2 and the inner ring 4 are configured as separately producible components. In other words, the separately producible components can be produced in different process steps and subsequently connected to one another to the base body 1. The separately producible components are made of sheet metal and are therefore producible by way of sheet metal processing. In alternative embodiments, only one of the separately producible components or a part of the separately producible components are made of sheet metal. The sheet metal can be, in particular, a steel sheet or a rolled metal sheet.

In particular, the separately producible components can be connected to one another by way of bonding and/or welding and/or riveting and/or clinching and/or clinch-bonding and/or rivet-bonding together into the base body 1. In particular, the separately producible components can be connected to one another by way of a hybrid joining process. In particular, the hybrid joining process can combine at least two of the methods described above for connecting two components. In particular, the outer shell 3.1, the polygonal ring 3.2 and the inner ring 4 are connected to the base plate 2. The outer shell 3.1 and the polygonal ring 3.2 are therein included by the outer ring 3.

A subregion 6 of the base body 1 is formed between the polygonal ring 3.2 and the inner ring 4 for accommodating an X-ray tube 32. Another subregion 7 of the base body 1 is formed between the polygonal ring 3.2 and the inner ring 4 for accommodating an X-ray detector 33. The inner ring 4 has a greater height in the subregion 6 of the X-ray tube 32 than in the subregion 7 of the X-ray detector 33. In particular, the inner ring 4 thus has a height difference between the two subregions 6, 7. Simulations for topology optimization have shown that on a rotation of the base body 1 about a rotation axis 40, a deformation of the base body 1 by centrifugal force occurs, in particular, in the subregion 6 of the X-ray tube 32. This deformation can be minimized in that the inner ring 4 is particularly stable there and/or is formed higher than in other regions of the base body 1. In the representation of the example embodiment of the base body 1, further radial struts between the inner ring 4 and the outer ring 3 are shown. These can also be configured as separate components and can be connected to the base plate 2, the outer ring 3 and/or the inner ring 4. These struts can serve for additional stability of the base body 1, in particular during a rotation.

In alternative embodiments, the height of the inner ring 4 can be constant. In other words, the inner ring 4 can have no height difference.

In an alternative embodiment, the outer shell 3.1 and the polygonal ring 3.2 form a common component. In other words, the outer ring 3 can be configured as one component.

FIG. 3 shows a further example embodiment of a base body 1 according to the invention of a computed tomography drum 31, comprising an outer ring 3 with an outer shell 3.1 and a polygonal ring 3.2, which form an intermediate space 5, in a radial sectional representation.

The representation of the example embodiment shows a radial cross-section and/or a radial sectional representation through the outer ring 3. The outer ring 3 here comprises an outer shell 3.1 and a polygonal ring 3.2. In particular, the outer shell 3.1 and the polygonal ring 3.2 are configured as separately producible components. In the drawing, three segments 3.2.1, 3.2.2, 3.2.3 of the polygonal ring 3.2 are shown. Formed between the polygonal ring 3.2 and the outer shell 3.1 is an intermediate space 5 and/or hollow space. The intermediate space 5 is fillable with a matrix 5.1. The matrix 5.1 can be configured, for example, as an aluminum honeycomb structure. In particular, the matrix 5.1 can be configured from a light but barely deformable material. In this way, a deformation of the base body 1 during a rotation about a rotation axis 40 can be minimized. Furthermore, the weight of the base body 1 can be reduced dependent upon the material of the matrix 5.1. At least two of the components (base plate 2, outer shell 3.1, polygonal ring 3.2) are configured as separately producible components. In particular, at least one of the components or all the components can consist of sheet metal. The sheet metal can be, in particular, a steel sheet or a rolled metal sheet.

In particular, the example embodiment can be combined with the example embodiment of FIG. 3.

FIG. 4 shows an example embodiment of a deep-drawn base plate 2 of a base body 1 according to the invention of a computed tomography drum 31.

The base plate 2 can be deep-drawn, in particular, from a round blank 24 or a sheet metal round blank. The round blank 24 can be configured, in particular, as a circular or annular or toroidal metal sheet. The base plate can be deep-drawn, in particular, by way of one or more punches, from the round blank 24.

In further processing steps and/or production steps, at least one outer ring 3 and an inner ring 3 can be placed on the deep-drawn base plate 2 and connected to the base plate 2 as described above. The outer ring can be configured as described in the description according to FIG. 3.

The base plate 2 comprises a plurality of beads 8. The beads 8 can be worked into the base plate 2 as a depression or an elevation. The beads 8 can be worked into the base plate 2, in particular, by way of deep-drawing. Alternatively, the beads 8 can be formed onto the base plate 2 by placement of a rolled-in metal sheet. The beads 8 are configured, in particular, so that they stabilize the base plate 2. In other words, the beads 8 reduce or prevent a deformation of the base plate 2.

In particular, the base plate 1 can be deep-drawn in such a way that it comprises interlocking elevations or depressions for the outer ring 3 and the inner ring 4. In particular, due to the interlocking elevations or depressions, the outer ring 3 and the inner ring 4 can be positioned precisely fitting on the base plate 2 and connected in position to the base plate 2.

FIG. 5 shows a production arrangement for deep-drawing a shell 23 of a base body 1 according to the invention of a computed tomography drum 31.

The shell 23 comprises a base plate 2 and an outer shell 3.1 of the base body 1. The shell 23 can be deep-drawn from a round blank 24, in particular, a sheet metal round blank. The round blank 24 can be configured, in particular, as a circular or annular or toroidal metal sheet. A diameter of the round blank 24 can correspond to at least the sum of a diameter of the base plate 2 and double the height of the outer shell 3.1. For this purpose, the round blank 24 can be drawn or pushed or pressed into the corresponding shape by way of a punch 20. In the example embodiment shown, two punches 20 are used for deep-drawing the shell 23. On deep-drawing, the metal sheet undergoes strain-hardening, which leads to enhanced stability of the shell 23.

To produce the base body 1, among other things, a polygonal ring 3.2 and/or an inner ring 4 can be inserted in the shell 23 in further production steps and connected to the base plate 2. Inserted means that the component to be inserted is positioned in the shell 23 and is connected to the base plate 2 and/or the outer shell 3.1. The connecting can take place after one of the processes described above in order to connect the separately produced components.

In particular, in embodiments, insertion of a complete polygonal ring 3.2 into the shell 23 can be dispensed with, if the shell 23 is constructed in a particularly stable manner. The shell 23 can be constructed in a particularly stable manner if a thick sheet metal round blank 24 is used for deep-drawing the shell 23. In particular, for deep-drawing, a sheet metal round blank with a thickness of up to 15 mm can be used. In particular, rather than a whole polygonal ring, at least one segment 3.2.1, 3.2.2, 3.2.3 of a polygonal ring 3.2 can be inserted into the shell 23 and connected at least to the base plate 2. In particular, the at least one segment 3.2.1, 3.2.2, 3.2.3 can also be connected to the outer shell 3.1. The at least one segment 3.2.1, 3.2.2, 3.2.3 can be configured, in particular, so that it provides a planar surface for fastening the X-ray tube 32 and/or the X-ray detector 33 in the base body 1. An intermediate space 5 between the at least one segment 3.2.1, 3.2.2, 3.2.3 of the polygonal ring and the outer shell 3.1 can be filled, as in the description relating to FIG. 3, with a matrix 5.1.

FIG. 6 shows a production arrangement for projection lengthening a shell 23 of a base body 1 of a computed tomography drum 31 according to an embodiment of the invention (drawing from Fritz Klocke, Fertigungsverfahren 4—Umformen, 2017, Springer Verlag, page 420, the entire contents of which are hereby incorporated herein by reference).

Similarly to the example embodiment of FIG. 5, the shell 23 comprises an outer shell 3.1 and a base plate 2. In the production process shown, the shell 23 is produced from a round blank 24, in particular, a sheet metal round blank, by way of the projection lengthening process. The round blank 24 can be configured as described in the description according to FIG. 5. During the projection lengthening process, an edge region of the round blank 24 is bent with a pressure roller 21 and a counterpressure roller 22 relative to an inner region of the round blank 24. The inner region of the round blank 24 corresponds to the round blank 24 without the edge region. In particular, the edge region can be bent such that the edge region is oriented perpendicularly to the remainder of the round blank 24. The edge region then forms, in particular, the outer shell 3.1. In particular, the inner region of the round blank 24 therein forms the base plate 2. Due to the bending, the sheet metal undergoes strain-hardening. Similarly to the description in relation to FIG. 5, the base body 1 can be made from the shell 23 in particular, among other things, by using at least one segment 3.2.1, 3.2.2, 3.2.3 of a polygonal ring 3.2 and/or a complete polygonal ring 3.2 and/or an inner ring 4. An intermediate space 5 between the at least one segment 3.2.1, 3.2.2, 3.2.3 of the polygonal ring and the outer shell 3.1 can be filled, as in the description relating to FIG. 3, with a matrix 5.1.

FIG. 7 shows a further example embodiment of a base body 1 according to the invention of a computed tomography drum 31 comprising a base plate 2, a polygonal ring 3.2 and a plurality of stiffening elements 9.

The polygonal ring 3.2 is connected, in particular, to the base plate 2. The polygonal ring 3.2 and the base plate 2 are therein configured, in particular, as separately producible components. In the example embodiment shown, an outer shell 3.1 for stabilization of the polygonal ring 3.2 is dispensed with. In order to stabilize the polygonal ring 3.2, stiffening elements 9 are arranged as angles between the base plate 2 and the polygonal ring 3.2. If the polygonal ring 3.2 is oriented perpendicularly to the base plate 2, the stiffening elements 9 encompass a right angle. In particular, each segment 3.2.1, 3.2.2, 3.2.3 can be supported with at least one stiffening element 9 relative to the base plate 2. The stiffening elements 9 can be connected, in particular, to the base plate 2 and the polygonal ring 3.2. The connection can be configured as described above. The stiffening elements 9 can be arranged, in particular, perpendicularly to the corresponding segment 3.2.1, 3.2.2, 3.2.3 of the polygonal ring 3.2 and perpendicularly to the base plate 2. The stiffening elements 9 can be oriented, in particular, from the viewpoint of the polygonal ring 3.2 radially outwardly. Alternatively, the stiffening elements 9 can be oriented from the viewpoint of the polygonal ring radially inwardly. The stiffening elements 9 can be configured, in particular, as separately producible components. At least one of the separately producible components can therein be made of sheet metal. In particular, all the separately producible components can consist of sheet metal. The base body 1 according to the example embodiment can, in particular, encompass an inner ring 4.

FIG. 8 shows a representation of a radial cross-section of the example embodiment of FIG. 7.

In the representation of the radial cross-section, a mode of functioning of the stiffening elements 9 is clear. The stiffening elements 9 support at least one segment 3.2.1, 3.2.2, 3.2.3 of the polygonal ring 3.2 against the base plate 2. For this purpose, the stiffening elements 9 are configured as angles. The stiffening elements 9 are configured, in particular, so that they form an angle enclosed by the at least one segment 3.2.1, 3.2.2, 3.2.3 of the polygonal ring 3.2 and the base plate 2. The stiffening elements 9 are connected, in particular, to the base plate 2 and the at least one segment 3.2.1, 3.2.2, 3.2.3 of the polygonal ring 3.2 as described above.

FIG. 9 shows a further example embodiment of a base body 1 of a computed tomography drum 31 comprising four sectors 10.1, 10.2, 10.3, 10.4.

In other words, the base body 1 is composed of four sectors 10.1, 10.2, 10.3, 10.4. In other words, the base body 1 is subdivided into four sectors 10.1, 10.2, 10.3, 10.4. A sector 10.1, 10.2, 10.3, 10.4 can be denoted by its opening angle 10.1.1, 10.2.1, 10.3.1, 10.4.1. The opening angle 10.1.1, 10.2.1, 10.3.1, 10.4.1 of the sectors 10.1, 10.2, 10.3, 10.4 that are included by the base body 1 can be equal in embodiments for all the sectors 10.1, 10.2, 10.3, 10.4. In alternative embodiments, the opening angle 10.1.1, 10.2.1, 10.3.1, 10.4.1 can be different from at least two sectors 10.1, 10.2, 10.3, 10.4. Each sector 10.1, 10.2, 10.3, 10.4 comprises a corresponding part or angular region of the base plate 2 and a corresponding part or angular region of the outer ring 3. The outer ring 3 can comprise an outer shell 3.1 and at least one segment 3.2.1, 3.2.2, 3.2.3 and/or at least a part of a segment 3.2.1, 3.2.2, 3.2.3 of a polygonal ring 3.2.

An intermediate space 5 between the outer shell 3.1 and the at least one segment 3.2.1, 3.2.2, 3.2.3 of the polygonal ring can be filled, as in the description relating to FIG. 3, with a matrix 5.1. Alternatively, the outer ring 3 can be configured in one piece.

In the example embodiment shown, a subregion of the base body 1, which is configured for the accommodation of an X-ray tube 32, forms a separate sector 10.1. Similarly, a subregion of the base body 1, which is configured for an accommodation of an X-ray detector 33 forms a separate sector 10.3. In particular, the subregions of the base body 1 form separate sectors 10.2, 10.4 between the two sectors 10.1, 10.3. In particular, therefore, the base body 1 is structurally subdivided into sectors 10.1, 10.2, 10.3, 10.4.

In alternative embodiments, the base body 1 can be subdivided into more or fewer than four sectors 10.1, 10.2, 10.3, 10.4. In particular, each of the sectors 10.1, 10.2, 10.3, 10.4 can be configured as a cast component or a cast part. In other words, each sector 10.1, 10.2, 10.3, 10.4 can be cast in a separate casting process and the cast components or cast parts or sectors 10.1, 10.2, 10.3, 10.4 can subsequently be assembled into the base body 1. In particular, the sectors 10.1, 10.2, 10.3, 10.4 can be produced or cast in a diecasting method or a permanent mold casting process. Alternatively, the sectors 10.1, 10.2, 10.3, 10.4 can be produced or cast in a sand casting process. In particular, the sectors can be cast from an aluminum-silicon casting alloy. In particular, the sectors 10.1, 10.2, 10.3, 10.4 can be joined to one another with a hybrid joining process. In other words, in each case, two sectors 10.1, 10.2, 10.3, 10.4 can be joined to one another with a hybrid joining process. In the hybrid joining process, two of the processes described above can be combined for joining two components. In particular, the sectors 10.1, 10.2, 10.3, 10.4 can be bonded and riveted to one another.

In the example embodiment shown, the base body 1 does not comprise an inner ring 4. This can be inserted in embodiments as described above and connected to the base plate 2. Alternatively, a part and/or an angular region of the inner ring 4 can be part of the corresponding cast component or cast part. In other words, the corresponding part of the inner ring 4 can be part of a sector 10.1, 10.2, 10.3, 10.4. In particular, no separate insertion and connection of the inner ring 4 is then necessary.

FIG. 10 shows an example embodiment of a sector 10 with an interlock 11.

In other words, a part of a sector 10 of a base body 1 is shown. The sector 10 therein comprises a portion and/or an angular region of a base plate 1 and a part and/or an angular region of an outer shell 3.1. In alternative embodiments, a sector 10 of the base body 1 can also comprise a corresponding portion and/or an angular region of an inner ring 4. In particular, a sector 10 of the base body 1 can be configured as described in relation to FIG. 9.

A subregion 11 of the sector 10 is configured interlocking and/or as an interlock. In other words, the subregion 11 of the sector 10 comprises an interlock. A counterpart to this interlocking subregion 11 is arranged on a second sector 10. In other words, a second sector 10 comprises an interlocking subregion 11 which is compatible with the interlocking subregion 11 of the sector 10 shown. The counterpart is configured such that it terminates interlockingly and/or flush with the interlock shown. In particular, the interlocking subregions 11 are configured such that both the sectors 10 terminate flush and/or can be connected flush. In other words, with the interlocking subregions 11 of two sectors 10, the two sectors 10 can be connected interlockingly and/or flush and/or precisely fitting.

In particular, each sector 10 comprises two interlocking subregions 11, so that it can be connected interlockingly on both sides to a second sector 10.

In particular, the interlocking subregions 11 are configured in such a way that it can be ensured that only those sectors 10 which are actually arranged in the base body 1 adjoining one another can be connected to one another. For this purpose, the interlocking subregions 11 of different sectors 10 can be configured differently. In particular, the interlocking subregions 11 can be configured differently with regard to their shape. In particular, only interlocking subregions 11 of sectors 10 which are to be connected to one another are configured compatible.

FIG. 11 shows a computed tomography device 30.

The computed tomography device 30 comprises a computed tomography drum 31. The computed tomography drum 31 comprises a base body 1 according to the example embodiments described above. The computed tomography drum 31 also comprises a fastening apparatus for an X-ray tube 32 and a fastening apparatus for an X-ray detector 33. The fastening apparatus for the X-ray tube 32 is therein arranged in the subregion 6 of the base body 1 which is configured to accommodate an X-ray tube 32. The fastening apparatus for the X-ray detector 33 is therein arranged in the subregion 7 of the base body 1 which is configured to accommodate an X-ray detector 33. The X-ray tube 32 and the X-ray detector 33 are arranged, in particular, opposite one another in the computed tomography drum 31. In particular, the X-ray tube 32 and der X-ray detector 33 are arranged with point symmetry relative to a rotation axis 40 of the computed tomography drum 31. In the representation according to FIG. 11, the X-ray tube 32 and the X-ray detector 33 are shown for the sake of clarity. Typically, the X-ray tube 32 and the X-ray detector 33 are covered by a cover or panel.

The computed tomography device 30 further comprises a drive 34 for a rotation of the computed tomography drum 31. In other words, the drive 34 is configured to rotate the computed tomography drum 31 about a rotation axis 40. Typically, the computed tomography drum 31 therein rotates at 250 rpm (rotations per minute).

The computed tomography device 30 also comprises a patient support 35. The patient support 35 is configured for positioning a patient 36 in the computed tomography drum 31. In particular, the patient 36 can be positioned by way of the patient support 35 in the rotation axis 40 of the computed tomography drum 31. In particular, the patient support 35 can be configured movably. In particular, the patient support 35 can be configured such that the patient 36 can be moved on the patient support 35 during an image scan on the rotation axis 40 through the computed tomography drum 31. In particular, the patient support 35 can be configured height-adjustable so that the patient 36 can climb onto and off the patient support as easily as possible.

Where it has not yet explicitly been set out, although useful and in the spirit of the invention, individual example embodiments, individual sub-aspects or features thereof can be combined or exchanged with one another without departing from the scope of the present invention. Advantages of the invention described in relation to an example embodiment also apply without explicit mention, where transferable, to other example embodiments.

Even if not explicitly stated, individual example embodiments, or individual sub-aspects or features of these example embodiments, can be combined with, or substituted for, one other, if this is practical and within the meaning of the invention, without departing from the present invention. Without being stated explicitly, advantages of the invention that are described with reference to one example embodiment also apply to other example embodiments, where transferable.

Of course, the embodiments of the method according to the invention and the imaging apparatus according to the invention described here should be understood as being example. Therefore, individual embodiments may be expanded by features of other embodiments. In particular, the sequence of the method steps of the method according to the invention should be understood as being example. The individual steps can also be performed in a different order or overlap partially or completely in terms of time.

The patent claims of the application are formulation proposals without prejudice for obtaining more extensive patent protection. The applicant reserves the right to claim even further combinations of features previously disclosed only in the description and/or drawings.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

None of the elements recited in the claims are intended to be a means-plus-function element within the meaning of 35 U.S.C. § 112(f) unless an element is expressly recited using the phrase "means for" or, in the case of a method claim, using the phrases "operation for" or "step for."

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A base body of a computed tomography drum, the base body comprising components including:
    a base plate;
    an outer ring having an outer shell and at least one segment of a polygonal ring; and
    an inner ring, the inner ring being arranged concentrically with the outer ring, and the outer ring and the inner ring being arranged on the base plate,
    wherein at least two of the components are configured as separately producible components,
    wherein two of the separately producible components are connected by way of at least one of bonding, welding, riveting, clinching, clinch-bonding or rivet-bonding.

2. The base body of claim 1, wherein at least one of the components includes sheet metal.

3. The base body of claim 1,
    wherein the outer shell and the at least one segment of the polygonal ring are configured to be separately producible.

4. The base body of claim 3, wherein the at least one segment of the polygonal ring is arranged concentrically in the outer shell.

5. The base body of claim 3, wherein at least one of the outer shell or the at least one segment of the polygonal ring is connected to the base plate.

6. The base body of claim 3, wherein an intermediate space between the at least one segment of the polygonal ring and the outer shell includes a matrix.

7. The base body of claim 1, wherein the base plate is made from a round blank.

8. The base body of claim 1, wherein beads are worked into the base plate by at least one of pressing or placement of a rolled-in metal sheet.

9. The base body claim 3, wherein the outer shell and the base plate form a shell of the base body, and wherein the shell is producible by deep-drawing a round blank.

10. The base body of claim 3, wherein the outer shell and the base plate form a shell of the base body, and wherein the shell is producible from a round blank by a projection lengthening process.

11. The base body of claim 1, wherein the base body forms subregions between the outer ring and the inner ring for accommodating an X-ray tube and an X-ray detector, wherein a height of the inner ring in a subregion in which the X-ray tube is arranged and a height of the inner ring in a subregion in which the X-ray detector is arranged have a relative height difference.

12. The base body of claim 3, wherein the outer ring comprises the polygonal ring and a plurality of stiffening elements, and
    wherein the plurality of stiffening elements support the polygonal ring against the base plate.

13. A base body of a computed tomography drum, the base body comprising:
    a base plate;
    an outer ring having an outer shell and at least one segment of a polygonal ring; and
    at least two mutually independently producible sectors, the at least two mutually independently producible sectors being cast components, wherein the at least two mutually independently producible sectors are connected together to the base body, and wherein each of the at least two mutually independently producible sectors includes a corresponding portion of the base plate and the outer ring.

14. The base body of claim 13, wherein two sectors, of the at least two mutually independently producible sectors, comprise interlocking subregions.

15. A computed tomography drum, comprising:
    the base body of claim 1;
    a fastening apparatus for an X-ray tube; and
    a fastening apparatus for an X-ray detector.

16. A computed tomography device, comprising:
    the computed tomography drum of claim 15;
    an X-ray tube;
    an X-ray detector;
    a drive to rotate the computed tomography drum; and
    a patient support.

17. The base body of claim 2,
    wherein the outer shell and the at least one segment of the polygonal ring are configured to be separately producible.

18. The base body of claim 17, wherein the at least one segment of the polygonal ring is arranged concentrically in the outer shell.

19. The base body of claim 4, wherein at least one of the outer shell or the at least one segment of the polygonal ring is connected to the base plate.

20. The base body of claim 4, wherein an intermediate space between the at least one segment of the polygonal ring and the outer shell includes a matrix.

21. The base body of claim 2, wherein the base body forms subregions between the outer ring and the inner ring for accommodating an X-ray tube and an X-ray detector, wherein a height of the inner ring in a subregion in which the X-ray tube is arranged and a height of the inner ring in a subregion in which the X-ray detector is arranged have a relative height difference.

22. The base body of claim 3, wherein the base body forms subregions between the outer ring and the inner ring for accommodating an X-ray tube and an X-ray detector, wherein a height of the inner ring in a subregion in which the X-ray tube is arranged and a height of the inner ring in a subregion in which the X-ray detector is arranged have a relative height difference.

23. A computed tomography drum, comprising:
   the base body of claim 13;
   a fastening apparatus for an X-ray tube; and
   a fastening apparatus for an X-ray detector.

24. A computed tomography device, comprising:
   the computed tomography drum of claim 23;
   an X-ray tube;
   an X-ray detector;
   a drive to rotate the computed tomography drum; and
   a patient support.

* * * * *